United States Patent [19]

Lormeau et al.

[11] Patent Number: 5,034,520

[45] Date of Patent: Jul. 23, 1991

[54] PROCESS FOR RECOVERING HEPARINIC OLIGOSACCHARIDES WITH AN AFFINITY FOR CELL GROWTH FACTORS

[75] Inventors: Jean-Claude Lormeau, Maromme; Maurice Petitou; Jean Choay, both of Paris, all of France

[73] Assignee: Sanofi, Paris, France

[21] Appl. No.: 39,471

[22] Filed: Apr. 16, 1987

[30] Foreign Application Priority Data

Apr. 17, 1986 [FR] France .................... 86 05546

[51] Int. Cl.[5] .................... C07H 1/00
[52] U.S. Cl. .................... 536/127; 536/21
[58] Field of Search .................... 536/21, 127; 514/56

[56] References Cited

U.S. PATENT DOCUMENTS

| | | | |
|---|---|---|---|
| 4,401,662 | 8/1983 | Lormeau et al. | 514/56 |
| 4,847,338 | 7/1989 | Linhardt et al. | 536/54 |

FOREIGN PATENT DOCUMENTS

| | | | |
|---|---|---|---|
| 0114589 | 8/1984 | European Pat. Off. | 514/56 |
| 0140781 | 5/1985 | European Pat. Off. | 514/56 |

OTHER PUBLICATIONS

Castellot et al., *The Journal of Cell Biology*, vol. 90, pp. 372-379 (Aug. 81).

Klagsbrun and Shing, *Proc. Natl. Acad. Sci. USA*, vol. 82, pp. 805-809 (Feb. 85).

Lobb and Fett, *Biochemistry*, vol. 23, No. 6, pp. 6295-6299 (Dec. 18, 1984).

Lobb et al., *Biochemistry*, vol. 29, No. 19, pp. 4969-4973 (Sep. 10, 1985).

Schreiber et al., [I], *The Journal of Cell Biology*, vol. 101, pp. 1623-1626 (Oct. 1985).

Schreiber et al. [U], *Proc. Natl. Acad. Sci. USA*, vol. 82, pp. 6138-6142 (Sep. 1985).

Thomas et al., *Proc. Natl. Acad. Sci. USA*, vol. 82, pp. 6409-6413 (Oct. 1985).

Maciag et al., *Chemical Abstracts* vol. 101, 1984.

*Primary Examiner*—Elli Peselev
*Attorney, Agent, or Firm*—Davis Hoxie Faithfull & Hapgood

[57] ABSTRACT

Figure 1:
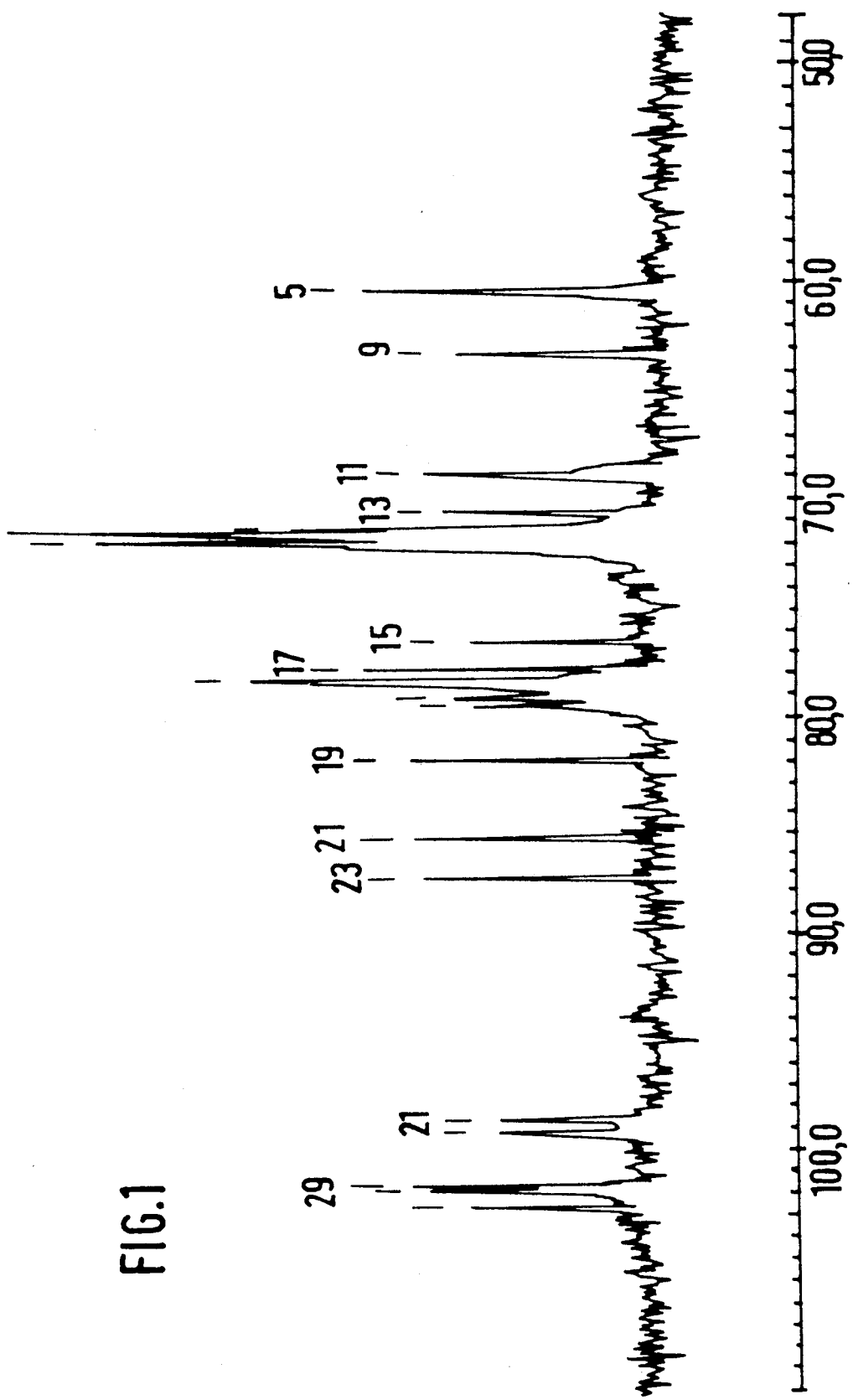

The oligosaccharides of the invention are composed essentially of chains:
- possessing a specific affinity for the anionic and cationic cell growth factor which recognize herparin,
- comprising at least one sequence of 5 residues matching those present in naturally occurring heparin and possessing a strongly anionic character such as that indicated in the NMR spectrum shown in FIG. 1, as well as their pharmacologically acceptable salts.

12 Claims, 14 Drawing Sheets

PROCESS FOR RECOVERING HEPARINIC OLIGOSACCHARIDES WITH AN AFFINITY FOR CELL GROWTH FACTORS

The subject of the invention is oligosaccharides of the heparinic type (heparin or heparan-sulfate) as well as their fragments which are capable of exerting an action on cell division and cell differentiation, their preparation and their therapeutic applications.

It is known that both heparin and heparan-sulfate are very heterogenous glycosaminoglycans. Thus, they are constituted of chains composed of alternating sugar residues, namely residues possessing the D-glucosamine structure and residues possessing a uronic acid structure (L-iduronic acid or D-glucuronic acid), or the reverse sequence. This basic structure may be regular, presenting a repeating sequence of disaccharide residues [D-glucosamine]-[L-iduronic acid], or irregular, the uronic acid residue being alternatively a residue of L-iduronic acid and D-glucuronic acid. Furthermore, the molecular weight of these chains may vary considerably from about 2,000 to 50,000. In addition, the ionic charge of residues with the same basic structure may vary according to their content of sulfate groups.

This heterogenous character is reflected in differences in the properties of the chains depending on the sequences they contain.

It is known that about one-third of the chains of heparin possess a binding site for ATIII (anti-thrombin III). Such chains are endowed with a more specific activity with regard to certain factors involved in blood coagulation.

The ⅔ of the heparin chains lacking the binding site for ATIII also lack the anticoagulant activity associated with this site.

The affinity of certain cell growth factors for heparin has also been reported. Use is made of this affinity for the purification of cell growth factors by affinity chromatography on columns of heparin-Sepharose ®.

The cell growth factors which exhibit an affinity for heparin are cationic or anionic polypeptides, of molecular weight of about 12,000 to 20,000, and which play a key role in cell physiology. In particular, they possess the property of being able to influence cell division and cell differentiation. This activity is exerted particularly on certain types of cells such as fibroblast cells and certain types of muscle cells. They are also implicated in the differentiation of neuronal cells.

These factors are called FGF, an abbreviation for "fibroblastic growth factor" or ECFG, an abbreviation for "endothelial cell growth factor" (see articles by J. Courty, Y. Courtois and D. Barritault in Biochimie 1984, vol. 66, p. 419–428 and Roy R. Lobb and James W. Fett in Biochemistry, vol. 23 No. 26, 1984, pp. 6295–6299).

It is to be noted that throughout the description and in the claims the terms "oligosaccharide and also glycosaminoglycan" includes naturally occurring materials, the oligosaccharide fragments obtained by depolymerisation of longer chains of glycosaminoglycans as well as oligo, or poly-saccharide sequences such as those obtained by synthesis. In these fragments and sequences, the residues at the reducing end and/or at the non-reducing end may be chemically modified with respect to the corresponding residue occurring in the naturally occurring chains of heparin or heparan sulfate. These modified residues will, however, also be designated by the term sugar residue or oligosaccharide residues throughout this description and in the claims.

The inventors made the surprising observation that the growth factors mentioned earlier possess a high affinity for only some oligosaccharide chains. The study of this affinity with a view to separating such chains led to the demonstration that families of oligosaccharides which are homogeneous with regard to their molecular weight are, in fact, constituted of a mixture of many anionic species of different charge and that the most highly anionic species possess regulatory activities with regard to cell division and cell differentiation. These findings are of great interest from a pharmacological point of view.

Thus, the aim of the invention is to furnish oligosaccharides of the heparin or heparan-sulfate type possessing a high affinity for cell growth factors capable of binding to heparin.

The aim of the invention is also to provide a procedure for the preparation of these oligosaccharides.

The invention also relates to application of these oligosaccharides for the preparation of drugs which act on cell division and cell differentiation.

The oligosaccharides of the invention are characterized by the fact that they are substances composed essentially of chains
possessing a specific affinity for anionic or cationic cell growth factors which recognize heparin
comprising at least one sequence of 5 residues matching those present in naturally occurring heparin and possessing very strongly anionic character such as that represented in the NMR spectrum shown in FIG. 1, as well as their pharmacologically acceptable salts.

These are products composed essentially of chains:
comprising the sequence of sugar residues of structure I:

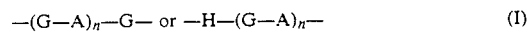

$$-(G-A)_n-G- \text{ or } -H-(G-A)_n- \qquad (I)$$

in which n is a number varying between 2 and 6

G-A corresponds to a disaccharide sequence of the structure (L-iduronic acid 2-O-sulfate)-(D-glucosamine NH-sulfate 6-O-sulfate)

G is a residue possessing the L-iduronic acid 2-O-sulfate structure,

A is a residue possessing the D-glucosamine NH-sulfate 6-O-sulfate structure, with specific affinity for the cationic or anionic cell growth factors which recognize heparin, and their pharmacologically acceptable salts.

In an advantageous manner, such glycosaminoglycans act on the mechanism of cell division and cell differentiation without interferring with the coagulation system, since they lack the binding site for AT III.

The disaccharide sequence GA corresponds more particularly to the structure II:

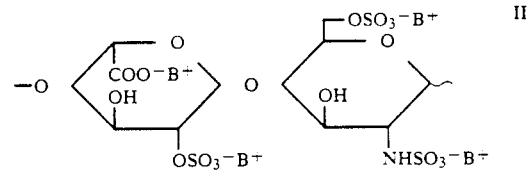

in which $B^+$ represents an organic or mineral cation giving rise to a physiologically acceptable salt.

The oligosaccharides of the invention correspond advantageously to the following formula III:

$$R(GA)_nR' \qquad \text{III}$$

in which

R represents either a hydrogen atom, or a disaccharide residue of the G-A type in which the G residue may possibly be modified chemically compared with the corresponding residue in the heparin chain, and R' represents either a hydrogen atom, or a disaccharide residue of the G-A type in which the A residue may possibly be modified chemically compared with the corresponding residue in the heparin chain, it being understood that the meanings of R and R' are such that the total number of sugar residues of the oligosaccharides, including the modified residues, does not exceed 14.

In a group of oligosaccharides of formula III above, the non-reducing ends and the reducing ends are composed of an intact sugar residue, i.e. a sugar residue bearing an OH group in position 4 or on the anomeric carbon atom in position 1, respectively.

In another group, the oligosaccharides contain at the non-reducing end and/or at the reducing end a different group from either a D-glucosamine residue or an L-iduronic acid residue. More particularly, this group is a sugar residue modified with respect to the corresponding residue of a heparin chain.

Given the agents usually used for the depolymerization of heparin, namely nitrous acid or heparinase, the residue at the reducing end is a residue possessing the 2,5-anhydromanno structure, advantageously 2,5-anhydromannitol or 2,5-anhydromannonic acid, and that at the non-reducing end is an $\alpha,\beta$ unsaturated uronic acid residue.

However, it will be quite clear to the specialist that organic chemical synthesis offers the possibility of introducing various organic radicals provided they do not modify the therapeutic effects of the oligosaccharide sequences defined above.

According to a preferred embodiment of the invention, the oligosaccharides are, in addition, homogeneous as regards their degree of polymerization, i.e. with regard to the number of residues constituting their chains.

A particularly useful oligosaccharide is constituted by a hexasaccharide. Such a hexasaccharide is composed of three repeating disaccharide sequences of the structure [L-iduronic acid 2-O sulfate]-[D-glucosamine-NH—sulfate 6-O-sulfate]. It is a compound represented by formula III in which R and R' both represent a hydrogen atom and n is equal to 3.

As a variant, the residues at the non-reducing end and/or at the reducing end are chemically modified compared with the corresponding residues present in heparin. The corresponding hexasaccharides are illustrated by formula III in which R and/or R' represent a modified sugar residue.

According to another aspect of the invention, the hexasaccharide corresponds to a compound contained in the fraction eluted in the volume between 32 l and 36 l of eluant from a gel filtration column. In this system, 60 g of precipitate, obtained by alcoholic precipitation of a nitrous acid depolymerization mixture of heparin, is taken up in 500 ml of 0.5M NaCl solution and loaded on to a 100 cm×25 cm column containing 45 liters of agarose-acrylamide, equilibarated with a 0.5M NaCl buffer, pH 6.0, and elution is carried out at a flow rate of 1500 ml/hour, the product obtained was separated by affinity chromatography on anionic FGF SEPHAROSE ® agarose gel using a 2.5 cm×6.5 cm column containing 30 ml of anionic FGF-SEPHAROSE ® agarose gel and equilibrated with a 0.01M Tris-HCL buffer, pH 7.4, containing 0.2M NaCl. 300 mg of the above fraction in a solution of 60 ml of the same buffer is loaded on to the column and elution is carried out with this buffer adjusted to 1M NaCl. The oligosaccharide is recovered by precipitation with ethanol from the fraction collected.

Another useful oligosaccharide is constituted by an octasaccharide. More particularly, this is an octasaccharide containing a hexasaccharide sequence such as that defined above. Compared with the corresponding structure found in heparin, the octasaccharide is constituted of non-modified residues or contains, as defined above for the hexasaccharide, a modified residue, at the non-reducing end and/or at the reducing end.

In conformity with another aspect of the invention, the octasaccharide is characterized in that it corresponds to:

a product contained in the fraction diluted in the volume between 28 l and 32 l of eluant from a gel filtration column. In this system, 60 g of precipitate, obtained by alcoholic precipitation of a nitrous acid depolymerization mixture of heparin, was taken up in 500 ml of 0.5M NaCl and loaded on to a 100 cm×25 cm column containing 45 liters of agarose-acrylamide and equilibrated with 0.5M NaCl buffer. Elution was carried out at a flow rate of 1500 ml/hour, the product obtained was separated by affinity chromatography on anionic FGF SEPHAROSE ® agarose gel using a 2.5 cm×6.5 cm column containing 30 ml of anionic FGF Sepharose ® and equilibrated with 0.01M Tris-HCL buffer, pH 7.4 containing 0.2M NaCl. 300 mg of the above fraction dissolved in 60 ml of the same buffer was loaded on to the column and elution was carried out with this buffer adjusted to 1M NaCl. The oligosaccharide was recovered from the fraction collected by precipitation with ethanol.

Other useful oligosaccharides are constituted by decasaccharides in which the residues at the reducing end or at the non-reducing end are chemically modified.

Such decasaccharides are characterized in that they are contained in the fraction eluted in the volume between 25 l and 28 l of eluant from a gel filtration column such as that described above for the isolation of the octasaccharide, and in that they are separated by affinity chromatography on anionic FGF SEPHAROSE ® agarose gel in accordance with the conditions indicated for the octasaccharide.

The oligosaccharides composed of chains containing 12 sugar residues, chemically modified at their ends as described above if necessary, are also useful compounds.

The oligosaccharides of the invention are prepared in the form of pharmacologically accepted salts, of which those of calcium, sodium, potassium and magnesium may be mentioned.

The invention also aims to provide a procedure for obtaining the oligosaccharides defined above.

This procedure is characterized by the addition of preparations of glycosaminoglycans of the heparin or heparan-sulfate type to a cationic or anionic cell growth factor advantageously bound to a support and by the utilization of buffers of the ionic strengths defined above to progressively elute the chains with no affinity for the growth factor, those with moderate affinity for the growth factor and then to recover the oligosaccharide chains tightly bound to the growth factor.

These steps make it possible to separate the strongly anionic chains from the mixture.

Starting preparations of glycosaminoglycans are used from which the chains or fragments possessing a binding site for AT III have been essentially removed. These preparations are composed of mixtures of naturally occurring chains of heparin or heparin-sulfate or depolymerization fragments of such native chains of heparin or heparan-sulfate, or mixtures of chains or fragments containing a maximum of 14 residues.

The addition of the preparations of glycosaminoglycans to the cell growth factor is carried out advantageously on a chromatography column containing the cationic or anionic growth factor equilibarated with a buffer. The cell growth factor is advantageously bound to a support. Suitable supports are those based on polysaccharides such as agarose. A convenient support for this type of application is constituted by an agarose gel marketed under the trade name of SEPHAROSE® agarose gel. Hemocompatible matrices may also be used such as grafted polystyrene, for example, and in particular the supports described in the patent application FR 2534486 of 15/10/1982 in the name of the Atomic Energy Commission, and the patent application FR 2553518 of 13/10/1983 in the name of CHOAY S.A. and C.N.R.S.

A satisfactory separation is effected by first passing a preparation of glycosaminoglycans over a matrix prepared beforehand by attaching to it a cationic or anionic cell growth factor and equilibrated with a buffer of an ionic strength corresponding to that of 0.2M NaCl. The oligosaccharide fraction retained is then eluted from the column as a result of a change in the ionic strength of the buffer corresponding to an increase of the NaCl concentration to between 1M and 2M.

According to one advantageous provision of the invention, the affinity chromatography step involving cell growth factor is carried out on a fraction of glycosaminoglycans which is homogeneous with regard to its molecular weight in order that a type of glycosaminoglycans of defined characteristics can be separated from such a fraction.

A fraction of glycosaminoglycans of this type is advantageously obtained by submitting a preparation of glycosaminoglycans such as that defined above to a gel filtration step.

By elution of the mixture loaded on to the top of the column of gel with an appropriate buffer, fractions of oligosaccharides, homogeneous with regard to their molecular weights, are successively recovered. Recourse is had to gels used in the standard manner for this type of operation, for example, to gels of the agarose-acrylamide type.

A satisfactory separation of such fractions is obtained by eluting with a buffer of ionic strength corresponding to that of an about 0.5M NaCl buffer.

The column effluents corresponding to the desired fraction of glycosaminoglycan are pooled and the fraction is precipitated by the addition of a mineral salt followed by an alcoholic solvent, ethanol in particular. The fraction recovered, while homogeneous from the point of view of the molecular weight of the chains, is very heterogeneous with regard to the ionic charge.

The preparation of glycosaminoglycans, formed of a mixture of chains to be fractionated, then to be separated by affinity chromatography by means of growth factors, or to be separated directly by means of these factors without prior fractionation, is carried out more particularly by depolymerization of heparin, followed by a fractionation step to separate the chains possessing the binding site for ATIII from the chains which lack this site.

The known procedures of depolymerization are based notably on the action of nitrous acid, heparinase, heparitinase or of periodate on heparin, depolymerization by nitrous acid or periodate being the most attractive from the point of view of an industrial procedure. The heparin used is crude heparin or heparin of pharmaceutical grade.

The depolymerization fragments used may possess at both the non-reducing end and at the reducing end a residue modified with respect to the corresponding structure found in heparin: these are represented, respectively, by an $\alpha,\beta$ unsaturated uronic acid residue in the case of depolymerization by means of heparinase, heparitinase or an $\alpha,\beta$ elimination, or a residue possessing a 2,5 anhydro-manno structure in the case of depolymerization by means of nitrous acid.

A preferred method of controlled, nitrous acid depolymerization corresponds to that which is the subject of the patent application FR No. 2,503,714 of 10/04/1981 in the name of the present applicant. According to the procedure described in that application, heparin and nitrous acid are allowed to react in an aqueous medium at respective concentrations such that all of the nitrous anions have been consumed when the desired degree of polymerization has been attained.

Advantageously, the 2,5 anydromannose groups which result from nitrous acid deamination are subsequently reduced to 2,5-anhydromannitol groups by a reducing agent such as sodium borohydride, or, alternatively, they are oxidized to 2,5-anhydromannonic acid groupings by an oxidizing agent such as permanganate, in particular, potassium permanganate.

The fractionation of the chains both possessing and lacking an ATIII binding site consists advantageously of an alcoholic fractionation, more particularly an ethanolic fractionation in the presence of a mineral salt leading to:

sub-fraction constituted of fragments of sizes corresponding mainly to 10, 12, 14, 16 and 18 sugar units of heparin, possessing the pentasaccharide binding site for antithrombine III, and endowed with a marked anti-factor Xa and a weak, overall anticoagulant activity, a sub-fraction constituted of fragments of sizes corresponding mainly to 2, 4, 6, 8 and 10 sugar units of heparin, almost completely lacking overall anticoagulant activity and exhibiting a very low anti-factor Xa activity.

Following a procedural variant, the glycosaminoglycans of the invention are obtained by means of ion exchange by using strongly basic anionic exchanges of the quaternary ammonium type and by applying an appropriate gradient to the ionic strength of the elution buffer.

The use of a buffer for equilibration and rinsing followed by an elution buffer having respectively the ionic strength corresponding to those of a 0.5M±0.1M NaCl and a 1 to 2M NaCl buffer leads to a satisfactory separation from the mixture of the chains with the desired affinity.

A satisfactory separation of oligosaccharide chains of the strongly anionic glycosaminoglycan type such as those described above is obtained by varying the ionic strength of the equilibration buffer from a value corresponding to a concentration of 0.4M NaCl to a value corresponding to a concentration of 1M NaCl, the gradient used being adapted to the type of glycosaminoglycans to be separated, particularly with respect to their chain lengths.

A pharmacological study of the glycosaminoglycans of the invention has demonstrated their properties on cell division and cell differentiation.

It is known that cell growth factors with an affinity for heparin act in particular by binding to several classes of cell receptors that are to be found in different types of cells.

As the inventors have observed, the glycosaminoglycans of the invention modify the activity of these growth factors.

Some cells are autocrine (in the sense defined by Sporn, M. B., Todaro G. J., in New Engl. J. Med., 303, 878–880, 1980) and permit a demonstration of the modulating potential, whether activator or inhibitor (in particular in relation to the phenotype, the state of differentiation of the cells under consideration), of the glycosaminoglycans of the invention on cell division and cell differentiation without the addition of growth factor.

Assays have been carried out on particular experimental models using cultures of endothelial cells of capillaries of mouse, beef and the human umbilical vein. They have shown a modulation of cellular multiplication compared with a control culture not containing glycosaminoglycans, or compared with a reference hexasaccharide lacking affinity for the anionic FGF.

The inhibitory role of certain steroids on neoangiogenesis in the presence of fragments of heparin is also known. Glycosaminoglycans of the invention, when administered with corticoids, have provided a favourable demonstration of an action of this type in the experimental model making use of the chorioallantoic membrane of the chicken and described by J. F. Folkman et al. in Science, 221, 719 (1983).

These favourable properties are not accompanied by any noxious effects.

Thus, the invention relates to the utilization of the glycosaminoglycans of the invention as modulators of the proliferation of endothelial cells. They may act either at low doses as inhibitors of the processes in which neoangiogenesis is pathological, or at higher doses, as stimulators of growth in certain processes in which the protection of growth factors is necessary and where regeneration is desirable.

As examples of pathological processes of neoangiogenesis, mention may be made of the retinopathies of diabetics, the development of metastases and psoriasis.

The products of the invention may also be used to inhibit embryonic development.

The utilization of the products of the invention may also be considered for the stimulation of the regeneration of endothelial lesions in certain cases or in cases of consecutive necroses arising from circulatory disorders, such as varicose ulcers. Their use may also be imagined for lesions of congenital or traumatic origin or in pathologies of acquired regeneration, particularly lesions to cardiac tissue after vascular accidents, such as infarcts.

The invention also relates to pharmaceutical preparations containing in their active principle an effective quantity of at least one of the glycosaminoglycans such as those defined above, in association with a pharmaceutical excipient.

Advantageous pharmaceutical preparations contained a highly anionic hexasaccharide described above, or the octasaccharide, the decasaccharide or the dodecasaccharide, or a mixture of them, in the form of their pharmacologically acceptable salts.

The active principle of these medicines comprises the glycosaminoglycan alone or, as a variant, associated with a cell growth factor processing an affinity for heparin. According to another variant, the glycosaminoglycan and the growth factor are used at the same time without having been combined beforehand.

In another advantageous application of the glycosaminoglycans of the invention, the latter may be used in combination with a steroid.

In view of their effects on cell division and cell differentiation, these pharmaceutical preparations can be used mainly in the following therapeutic indications:

stimulation of the repair of muscle tissues after lesions, in particular those of congenital or traumatic origin; of cardiac tissue after vascular lesions, such as infarcts; cutaneous tissue after lesions, especially those of traumatic origin, acceleration of healing after lesions of traumatic origin, alone or in combination with steroids, inhibition of processes in which neoangiogenesis is pathological, such as retinopathies of diabetics, development of metastases and psoriasis.

The pharmaceutical preparations of the invention can be administered in different forms.

These pharmaceutical forms may be hydrated when the glycosaminoglycan is used alone to constitute the active principle. They must be anhydrous when the active principle contains a growth factor. This latter is present at a concentration of 1 to 200 µg per unit dose, advantageously 25 to 100 µg.

For administration by the oral route, use may be made in particular of capsules, lozenges, tablets, pills and liposomes. These preparations advantageously contain from 50 mg to 5 g per unit dose, preferably from 50 to 250 mg for capsules, lozenges and pills.

Other forms of administration of the products of the invention are constituted by sprays, pomades, creams, and possibly aerosols, the concentration of the active product being of the order of 0.5% to 10%.

In an advantageous manner, the products of the invention are administered as pharmaceutical preparations which may be injected intravenously, subcutaneously or intra-muscularly, as sterile or sterilizable solutions.

In an advantageous manner, the products of the invention are utilized in combination with growth factors, in particular in preparations for topical use.

The solutions intended for intravenous, subcutaneous or intramuscular administration advantageously contain 10 to 250 mg/ml of mixtures of glycosaminoglycans, preferably from 10 to 100 mg/ml, for example 100 mg/ml when these solutions are intended for injection by the subcutaneous route. They may contain, for example, from 10 mg to 500 mg, in particular 150 mg/ml of glycosaminoglycans, when they are intended for injection by the intravenous route or by perfusion.

Advantageously, such pharmaceutical preparations are available in a form of ready-to-use disposable syringes.

In order to illustrate the invention, an example of the dosage which may be used in man is given below: this dosage comprises, for example, the administration to the patient of about 30 to 500 mg/day in one or several doses by the subcutaneous or intravenous route. By the intravenous route, about 150 mg/day are administered whereas the quantities injected by perfusion may amount to several tens of ml. These administrations are performed in a discontinuous manner at regular intervals or continuously by perfusion. The doses can, of course, be adjusted for each patient in the light of preceding analyses and the results obtained, the nature of the disorders from which he is suffering and his general state of health.

The pharmaceutical preparations described above may include, in addition, a compound of the steroid type, provided the quantities do not exceed tolerable doses. In particular, the quantity of the steroid may be such that the dose administered to the patient does not exceed 5 mg/kg/day.

In other preparations, this dose is higher. However, the doses may be high when the steroid derivatives administered have lost their hormonal activity.

The invention also relates to biological reagents, the active principles of which are constituted by the preparations of glycosaminoglycans such as those defined above. These biological reagents may be utilized as references or calibration standards in studies of the possibly antitumoral properties of other substances, in particular, in tests in which the techniques which have been described in the preceding examples are applied.

The glycosaminoglycans of the invention may be bound in a conventional manner to insoluble gels and to other inert, conventional, insoluble supports or matrices in order to furnish support for affinity chromatography which enables separations to be carried out. As suitable supports, mention will be made of those constituted by a polysaccharide, in particular a gel of agarose such as that marketed under the trade name of Sepharose® and, generally speaking, hydrophilic, insoluble supports on to which aminoethyl groups have been grafted, such as aminoethyl-cellulose, aminoethyl-polyacrylamide and aminoethyl-agarose. The glycosaminoglycans are bound to these supports by reductive amination in a basic medium in the presence of sodium cyanoborohydride, for example, according to the following reaction scheme:

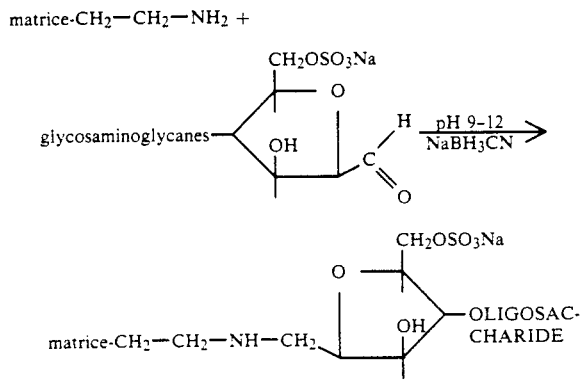

The matrices thus obtained are packed in columns.

The placing in contact of cationic or anionic cell growth factors with the glycosaminoglycans of the invention bound to supports or matrices provides means for selectively retaining cell growth factors. These bound glycosaminoglycans can thus be used as ligands to purify cell growth factors or to reduce the concentration of these factors in a given medium.

In an advantageous manner, the separation of growth factors is performed as follows:

the crude extract or the solution containing the cell growth factor to be retained is allowed to percolate into the column at neutral pH in a buffer of low ionic strength: 0.1 to 0.6M NaCl. The column is rinsed with the same buffer until proteins can no longer be detected in the effluent. The cell growth factor retained on the matrix is eluted either directly with a buffer of neutral pH and of an ionic strength given by 0.8 to 2M NaCl, or by a continuous gradient of ionic strength increasing from 0.8M to 2M NaCl.

These growth factors may originate either directly from biological samples or from preparations which have previously been subjected to certain purification steps.

Other characteristics and advantages of the invention are reported in the examples which follow concerning the preparation of different glycosaminoglycans and the results of pharmacological tests.

Figure 2:
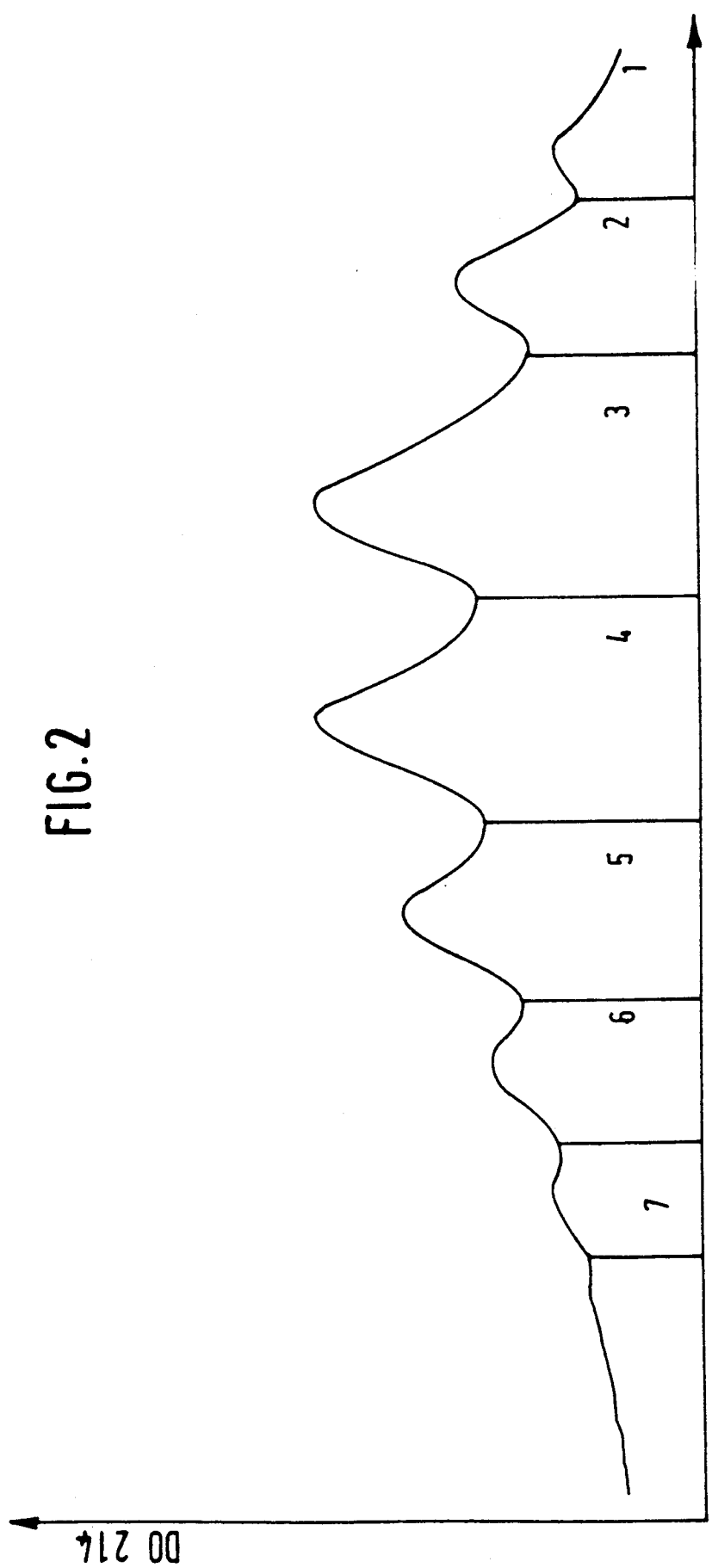
Figure 3:
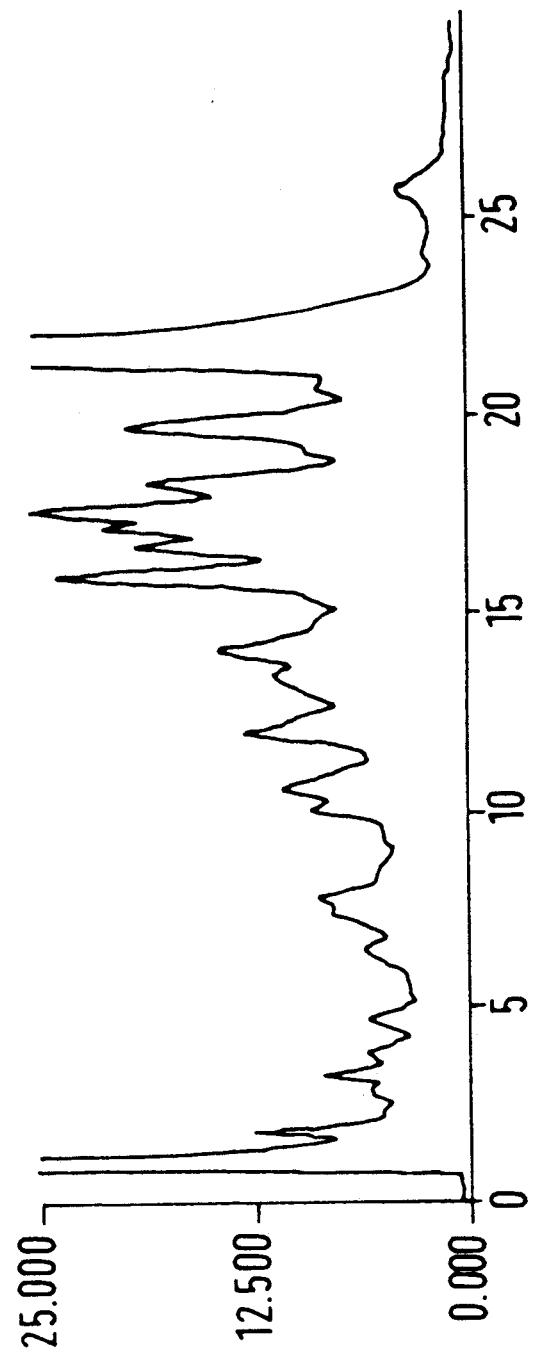
Figure 4:
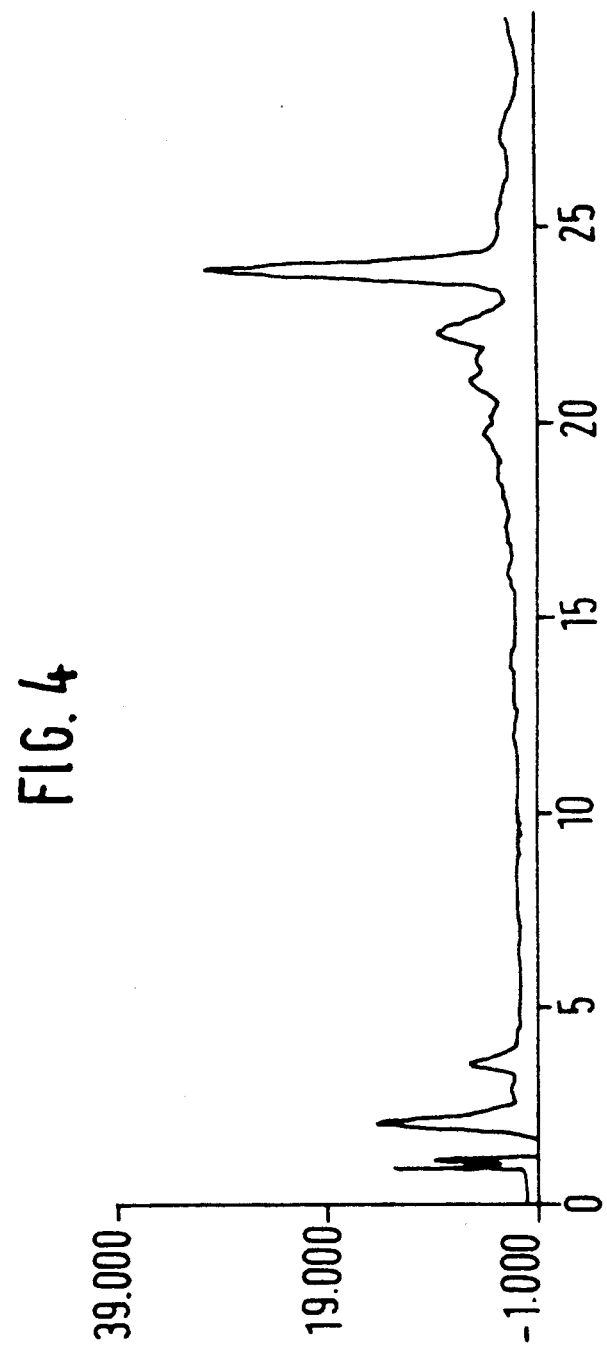
Figure 5:
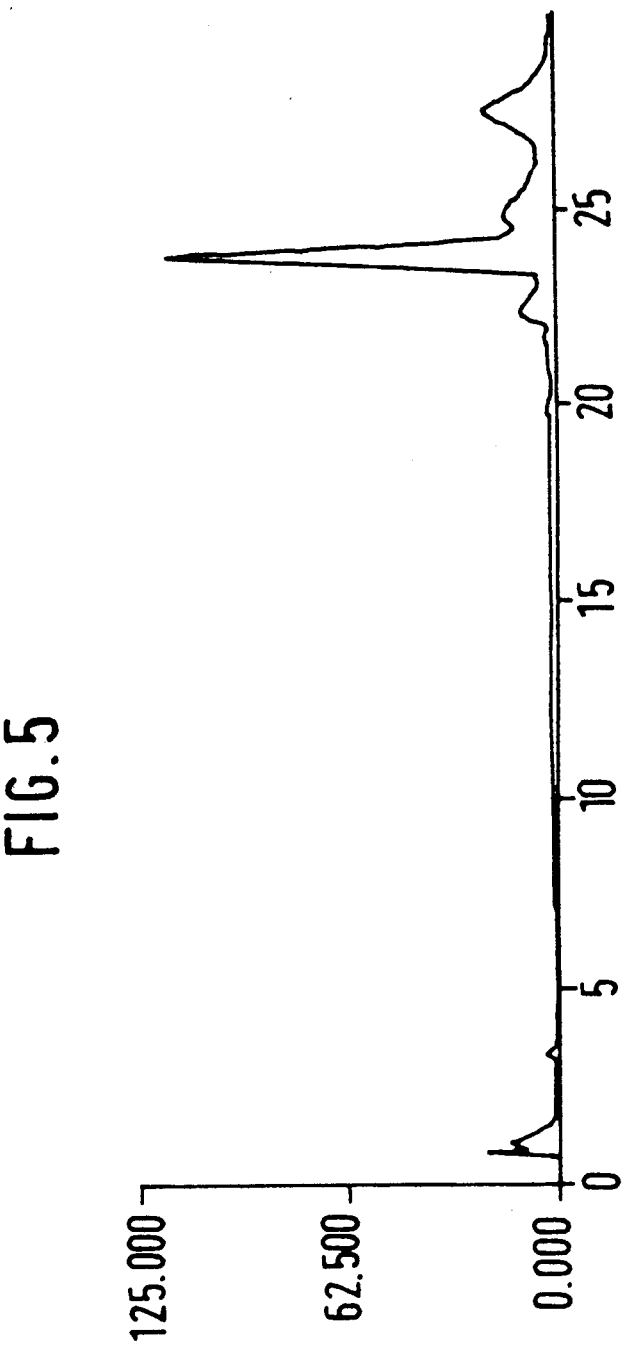
Figure 6:
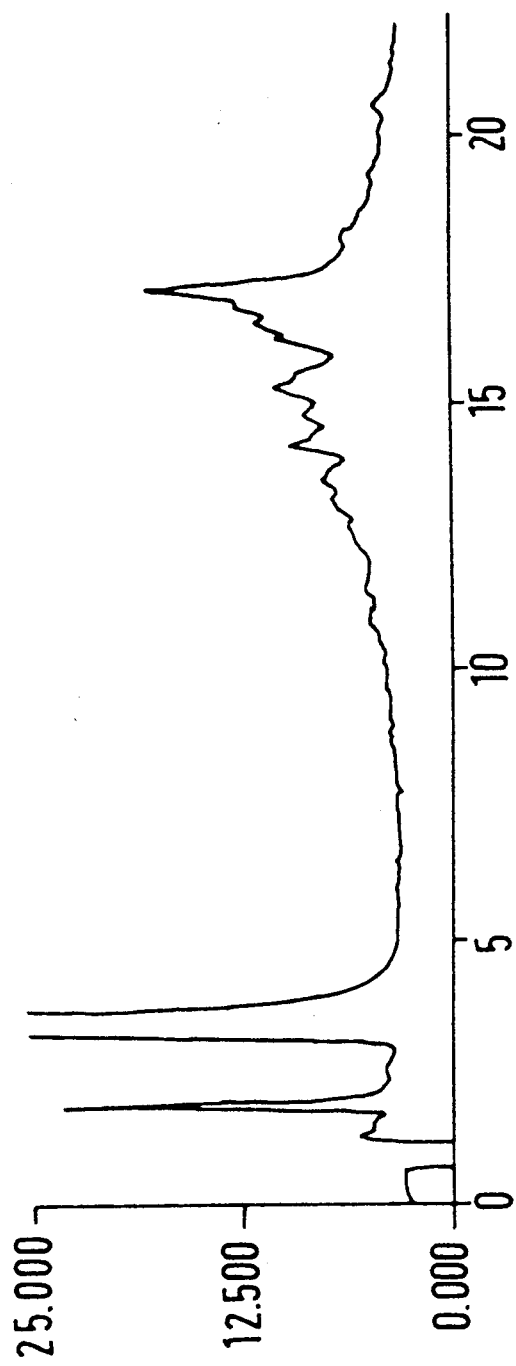
Figure 7:
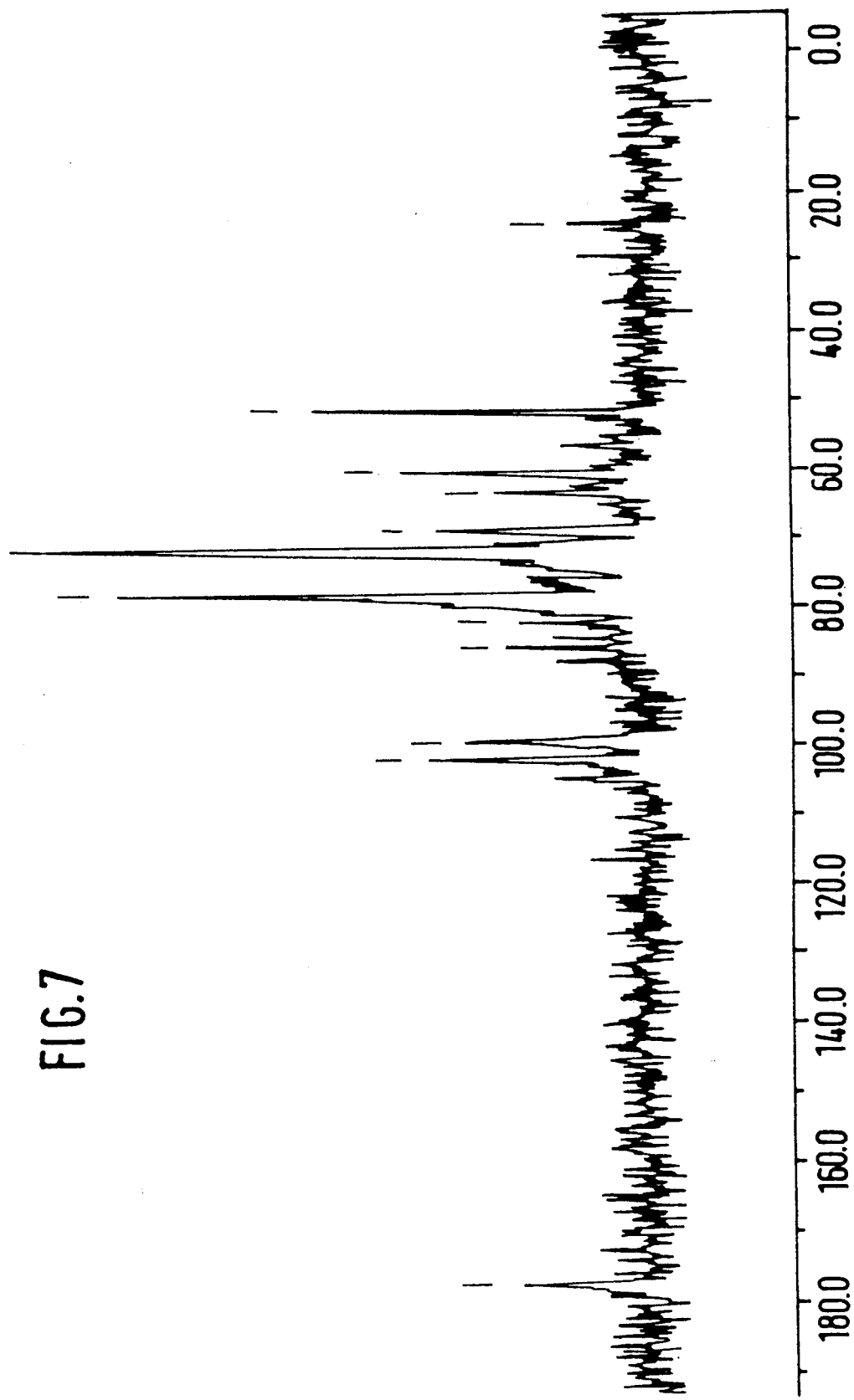
Figure 8:
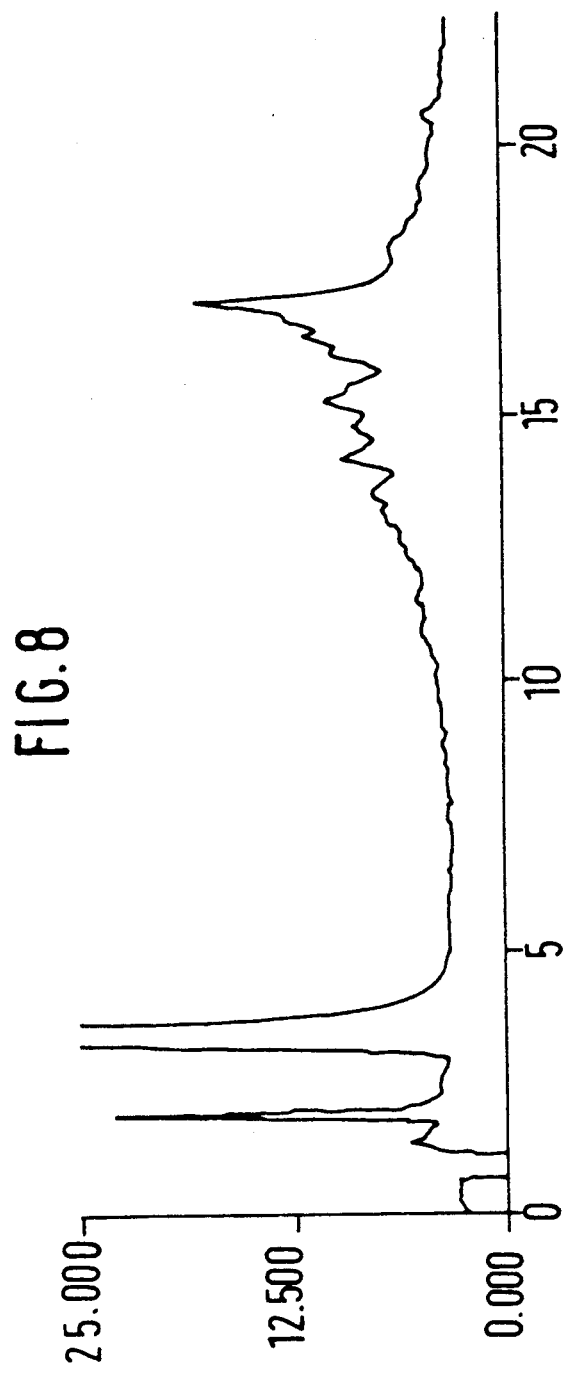
Figure 9:
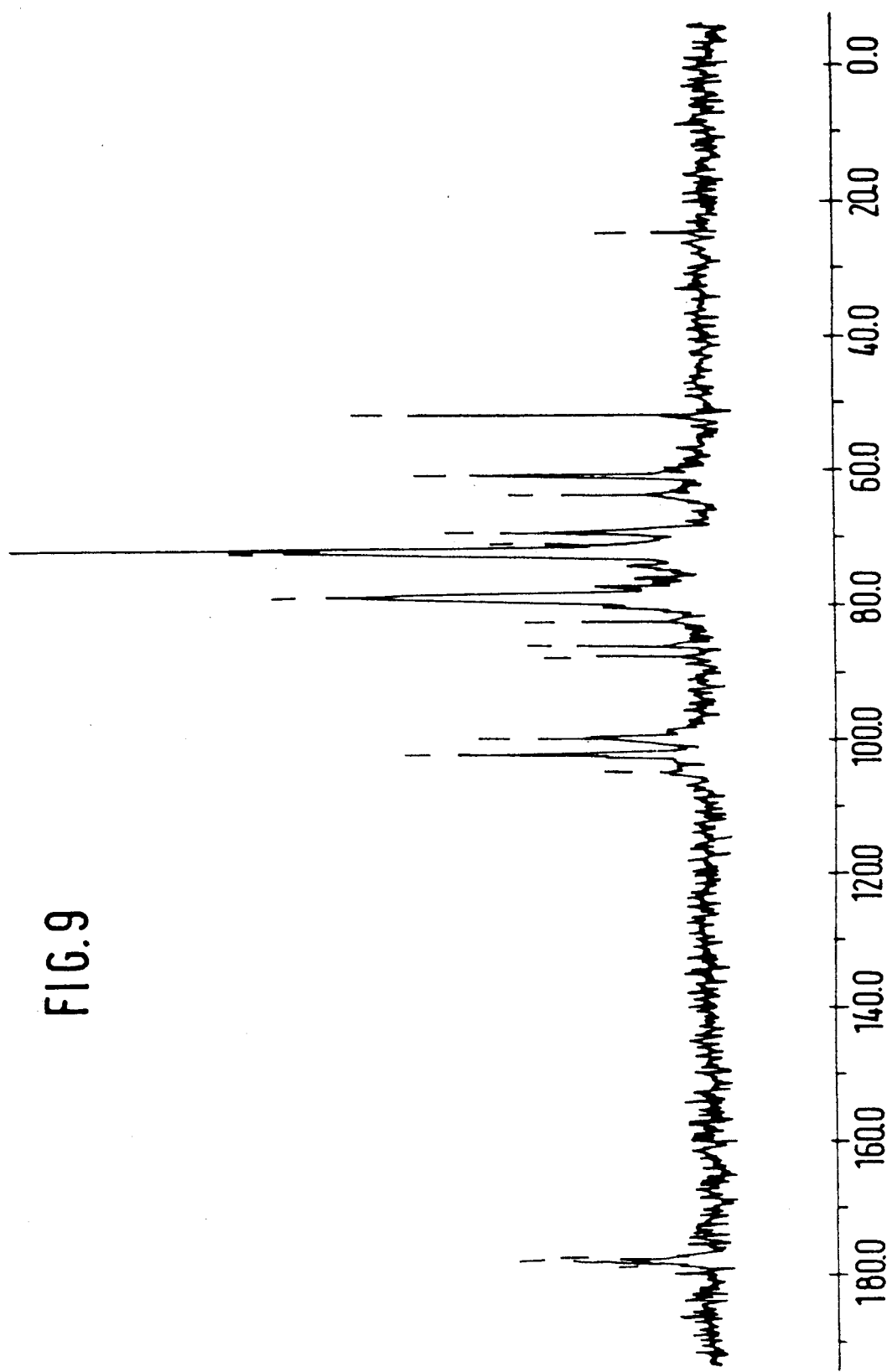

Reference will also be made to the FIGS. 1 to 13, which represent respectively:

FIG. 1, the $^{13}C$ NMR spectrum of a highly anionic hexasaccharide;

FIG. 2, the elution profile corresponding to the gel filtration of a nitrous acid depolymerization mixture;

FIG. 3, the elution profile from an ion exchange column of the hexasaccharide fraction recovered after gel filtration;

FIG. 4, the elution profile from an ion exchange column of the hexasaccharide isolated by chromatography on FGF-SEPHAROSE® agarose gel;

FIG. 5, the elution profile from an ion exchange column of the hexasaccharide obtained by chromatography on an ion exchange column (rechromatography);

FIG. 6, the elution profile from an ion exchange column of a mixture of octasaccharides;

FIG. 7, the $^{13}C$ NMR spectrum of this mixture of octasaccharides;

FIG. 8, the elution profile from an ion exchange column of a mixture of decasaccharides;

FIG. 9, the $^{13}C$ NMR spectrum of this mixture of decasaccharides;

FIGS. 10 to 13, the radioactivity plots in cpm as a function of the dose of products tested in ng obtained respectively with anionic FGF alone, a hexasaccharide alone or with an anionic FGF, another hexasaccharide alone or with anionic FGF, a control substance lacking affinity for the anionic FGF, used alone or with anionic FGF, and FIGS. 14A-D represent the plots for the proliferation of human endothelial cells in culture under different conditions.

EXAMPLE 1

A—Depolymerization 500 g of injectable heparin, in the form of its sodium salt are dissolved in 4500 ml of demineralized water at 18° C. (concentration about 11% W/V).

The solution obtained is stirred vigorously and its pH is brought to 2.5 by the addition of concentrated hydrochloric acid. 15 g of sodium nitrate dissolved in 300 ml of water are then added. (q.s.p. 0.043M final). The pH of the reaction is adjusted to 2.5 by the addition of concentrated hydrochloric acid and the total volume of the solution is made up to 5000 ml in order to give a final concentration of heparin of 10% W/V. The reaction is allowed to continue for 45 minutes. At the end of this period, the absence of residual nitrous ions in the reaction solution is verified by means of indicator paper impregnated with starch-potassium iodide (a blue-violet colour develops in the presence of $NO_2^-$ ions).

If nitrous ions are detected, the reaction is allowed to proceed until these ions have totally disappeared as signalled by the absence of reaction to starch-iodide paper, checks being made every 3 to 4 minutes.

When the spot checks have become negative, the reaction is considered to be complete. The pH of the solution is the raised to 10 by means of concentrated sodium hydroxide solution and 5 g of sodium borohydride are added. The solution is then stirred for 15 hours. Unreacted sodium borohydride is destroyed by lowering the pH to 3.0 by means of concentrated hydrochloric acid: the solution is stirred for 15 minutes and then it is readjusted to pH 7.0 by means of concentrated sodium hydroxide solution.

The products of the reaction are recovered by the addition of 10 l of ethanol and leaving the mixture to stand for 48 hours. The supernatant is then decanted.

B—Fractionation

The precipitate is redissolved in 9 liters of demineralized water (concentration 5% W/V based on the weight of the starting heparin). 100 g of sodium chloride are added and the pH of the solution is lowered to 3.8 by the addition of concentrated hydrochloric acid. The volume of the solution is adjusted to exactly 10 liters by means of demineralized water and 10 liters of ethanol are added with vigorous stirring. The mixture is left to stand for 48 hours. The supernatant is siphoned off and the pH is adjusted to 7.0 by means of 5N sodium hydorxide solution. 19 liters of ethanol are added. The mixture is left to stand for 48 hours. The supernatant is removed by siphoning. The precipitate is recovered, washed wit ethanol, broken up and dried in a vacuum. In this way 120 g of a mixture of oligosaccharides is obtained.

C—Gel Filtration 60 g of the mixture obtained are dissolved in 500 ml of 0.5M NaCl and loaded on to the top of a column of ULTRAGEL AcA 202 ® agarose-acrylamide gel. The column is eluted at a flow rate of 1500 ml/hour with 0.5M NaCl buffer.

The UV absorption at 214 nm of the effluent is recorded continuously. The elution profile obtained is shown in FIG. 2. 7 fractions are pooled and each is precipitated with 2 volumes of ethanol. The fractions are characterized as follows:

| Fraction No. | 1 | 2 | 3 | 4 | 5 | 6 | 7 |
| --- | --- | --- | --- | --- | --- | --- | --- |
| Volume (liter) | 2,1 | 2,2 | 4,1 | 3,9 | 3,3 | 2,5 | 1,8 |
| Elution volume (liters) | 41–39 | 39–36 | 36–32 | 32–28 | 28–25 | 25–22 | 22–20 |
| Dry weight of product* | 1,2 g | 5,6 g | 12 g | 9,8 g | 8 g | 6,2 g | 1,5 g |
| Nature | di-saccharide | tetra | hexa | octa | deca | dodeca | tetradeca |

*The product obtained by alcoholic precipitation is centrifuged and dried in a vacuum at 60° C. for about 30 hours.

The elution profile of the hexasaccharide fraction from an ion exchange column is shown in FIG. 3 in which the retention time is shown on the abscissa and the amounts of product in the eluate on the ordinate. The eluant is carried out by using a ion-exchange chromatography column of MONO-Q ®, marketed by Pharmacia in conjunction with a NaCl gradient of from 0.5 to 1.5M, the flow rate being 1 ml/mn. Detection is carried out by measuring the absorption at 214 nm. Visual examination of this elution profile shows the heterogeneity of the fraction.

D—Affinity Chromatograph on FGF-SEPHAROSE ® agarose gel

The anionic FGF is prepared from beef brain according to the technique of Roy R. Lobb and James W. Fett, Biochemistry vol. 23, No. 26, 1984, pp. 6295–6299.

45 mg of anionic FGF are bound to 30 ml of SEPHAROSE ® agarose gel according to the technique of P. M. Cuatrecasas, M. Wilchek and C. B. Anfinsen, Proc. Nat. Acad. Sci. U.S. 61 (1968), 636.

The 30 ml of FGF-SEPHAROSE ® agarose gel thus obtained are placed in a column (2.5 cm × 6.5 cm), and equilibrated with 0.01M Tris-HCl buffer pH 7.4 containing 0.2M NaCl (called hereafter buffer I).

300 mg of the hexasaccharide fraction dissolved in 60 ml of buffer I are loaded onto the column of FRG-SEPAHAROSE ® agarose gel; the column is then washed with 600 ml of buffer I at a flow rate of 60 ml per hour. The column is finally eluted with buffer I adjusted to 1M NaCl. The 18 ml of eluate containing oligosaccharides are pooled and precipitated by the addition of 108 ml of absolute ethanol. This leads to the recovery of 0.15 mg of a hexasaccharide, the elution profile of which from an ion exchange column is presented in FIG. 4. This product will henceforth be referred to as IC 1696.

The characteristics of the $^{13}C$ NMR spectrum of the hexasaccharide are given in FIG. 1, the following symbols being used to represent the 6 constitutive residues: $G_1\ H_1\ G_2\ H_2\ G_3\ AM_3$.

The spectrum is recorded on a solution of this substance dissolved in deuteratred water at 25 MHz, reference for the shift measurements: TSP, 3-(trimethylsilyl) propionic acid, sodium salt.

| ppm | Signal | Attribution | More general attribution* | |
|---|---|---|---|---|
| 60,5 | 5 | C-2 of $H_1 + H_2$ | C-2 | of the glucosamine N-sulfate group |
| 63,3 | 9 | C-1 of $AM_3$ | C-1 | of the anhydromannitol group |
| 68,9 | 11 | C-6 of $H_1 + H_2$ | C-6 | of the glucosamine N-sulfate-6-sulfate group |
| 70,7 | 13 | C-6 of $AM_3$ | C-6 | of the anhydromannitol 6-sulfate group |
| 77,8 | 17 | C-3 of $AM_3$ | C-3 | of the anhydromannitol group |
| 82,0 | 19 | C-5 of $AM_3$ | C-5 | of the anhydromannitol group |
| 85,6 | 21 | C-2 of $AM_3$ | C-2 | of the anhydromannitol group |
| 87,5 | 23 | C-4 of $AM_3$ | C-4 | of the anhydromannitol group |
| 98,6<br>99,2 | 27 | C-1 of $H_1 + H_2$ | C-1 | of the glucosamine-<br>N-sulfate group |
| 102,6<br>101,8<br>101,6 | 29 | C-1 of $G_1 + G_2 + G_3$ | C-1 | of the iduronic acid 2-sulfate group |

*i.e. with respect to known signals in this region of heparin.

EXAMPLE 2

The procedure was carried out in a manner similar to that described in Example 1, a different batch of injectable heparin being used.

115 g of a mixture of oligosaccharides are finally recovered. 60 g of this mixture are subjected to gel filtration under the same conditions as those described in Example 1.

The characteristics of the fractions recovered are presented in the table below:

| Fraction No. | 1 | 2 | 3 | 4 | 5 | 6 | 7 |
|---|---|---|---|---|---|---|---|
| Volume (liter) | 2,2 | 2,2 | 3,1 | 2,0 | 3,4 | 3,1 | 2 |
| Dry weight of product | 4,6 g | 1,9 g | 11,8 g | 1,7 g | 10,2 g | 7,9 g | 6,0 g |
| Nature | tetra saccharide | mixture of tetra + hexa | hexasaccharide | mixture of hexa + octa | octasaccharide | decasaccharide | dodecasaccharide |

300 mg of fraction 2 (tetra-hexa mixture) are subjected to affinity chromatography on FGF-SEPHAROSE ® agarose gel. Thus, 0.11 mg of product is finally obtained and referred to as IC 1697.

300 mg of the hexasaccharide fraction are subjected to affinity chromatography on FRG-SEPHAROSE ® agarose gel. In this way, 0.22 mg of a product is obtained, the elution profile of which from an ion exchange column corresponds to that presented in FIG. 4.

EXAMPLE 3

1.5 g of the hexasaccharide fraction 3 are loaded on to anion exchange column of Q SEPHAROSE ® agarose gel (170 ml, 2.5 cm×35 cm) equilibrated with 0.4M NaCl buffer.

The column is rinsed with the 0.6M buffer until oligosaccharides substances no longer appear in the effluent (rinsing volume: 3.5 liters). The oligosaccharides which are not absorbed, and which are recuperated on rinsing, correspond to the compound lacking affinity for the anionic FGF and will be called hereafter p38EXH13.

The column is then eluted with 1M NaCl buffer and the 120 ml of eluate containing oligosaccharides are pooled and precipitated by the addition of 720 ml of ethanol. In this way, 80 mg of a product are obtained, the elution profile of which from an ion exchange column is presented in FIG. 5.

EXAMPLE 4

Procedure for the separation of a strongly anionic hexasaccharide for affinity chromatography on cationic FGF-SEPHAROSE ® agarose gel.

The preparation of cationic FGF from beef brain and the attachment of cationic FGF to SEPHAROSE ® agarose gel are carried out according to the same procedures as those described for anionic FGF.

A column (1.6 cm×5 cm) containing 10 ml of cationic FGF-SEPHAROSE ® agarose gel (1.5 mg of cationic FGF per ml of Sepharose) is equilibrated with buffer I.

100 mg of hexasaccharide (prepared as described in example 1) dissolved in 20 ml of buffer I are loaded onto the column. The column is washed with 200 ml of buffer I, then eluted with buffer I adjusted to 2M NaCl. The 10 ml of eluate containing the oligosaccharides are pooled and the oligosaccharides are precipitated by the addition of 50 ml of absolute ethanol. In this way 0.050 mg of a hexasaccharide are recovered, the elution profile of which from an ion exchange column corresponds to that shown in FIG. 4.

EXAMPLE 5

Variants for the preparation of a depolymerization mixture containing the oligosaccharides of the invention:

Preparation of Oligosaccharides by Periodate Degradation 10 g of heparin are dissolved in 200 ml of demineralized water.

A quantity of sodium metaperiodate is added sufficient to give a final molarity of 0.25M, i.e. 10.7 g, and the pH of the solution is lowered to 3.0 by the addition of 5N HCl.

The solution is allowed to stand in the dark at 25° C. for 48 hours.

The pH is brought to 7 by the addition of 5N sodium hydroxide solution and 300 ml of absolute ethanol are added. The precipitate formed is recovered, broken up, washed with ethanol and acetone, and finally dried in a vacuum at 60° C.

It is redissolved in 120 ml of 0.2N sodium hydroxide solution containing 2 ml of sodium borohydride per ml. The solution is stirred for 15 hours at room temperature. The pH is adjusted to 4 by the addition of 5N HCl, and then brought again to 7 by the addition of 5N sodium hydroxide solution. 200 ml of absolute ethanol are added. The precipitate formed is centrifuged, broken up, washed with ethanol and acetone, and dried in a vacuum at 60° C.

Thus are obtained 6.4 g of a mixture of oligosaccharides. This mixture is subjected to a gel filtration step on ULTRAGEL AcA 202 ® agarose-acrylamide gel under the conditions described in example 1.

Preparation of the Oligosaccharides by Means of the Enzymes Heparinase and Heparitinase Heparinase and heparitinase are extracted from *Flavobacterium heparinum* and purified according to the method described by P. Hovingh and A. Linker, J. Biol. Chem. vol. 245 No. 22, 1970, pp. 6170–6175.

Depolymerization by Means of Heparinase 10 g of heparin are dissolved in 500 ml of 0.1M acetate buffer, pH 7.0, containing 0.01M $CaCl_2$.

The solution is placed in a water-bath at 30° C. and 2.5 mg of pure heparinase are added.

Incubation is allowed to proceed for 24 hours at 30° C. 1200 ml of absolute ethanol are added.

The precipitate formed is recovered by centrifugation, washed with ethanol and dried in a vacuum at 60° C.

7.1 g of a mixture of oligosaccharides is obtained which is subsequently subjected to gel filtration on ULTRAGEL AcA 202 ® agarose-acrylamide gel under the conditions described in example 1.

Depolymerization by Means of Heparitinase 10 g of heparin are dissolved in 500 ml of 0.1M acetate buffer, pH 7.0, containing 0.01M $CaCl_2$.

The solution is placed in a water-bath at 40° C. and 5 mg of pure heparitinase are added. The incubation is allowed to proceed for 10 hours at 40° C., then 3 mg of pure heparitinase are added. The incubation is continued for a further 6 hours and a further 3 mg of heparitinase are then added. 10 hours after this last addition, the products of the reaction are precipitated by the addition of 1200 ml of ethanol.

The precipitate formed is recovered by centrifugation, washed with ethanol and dried in a vacuum at 60° C.

6.8 g of a mixture of oligosaccharides is obtained which is subsequently subjected to gel filtration on Ultrogel AcA 202 ® under the conditions described in example 1.

EXAMPLE 6

Preparation of octasaccharides with high affinity for the anionic FGF by affinity chromatography on FGF-SEPHAROSE ® agarose gel.

The chromatographic column is prepared as described in example 1 D.

300 mg of the octasaccharide fraction such as that obtained in example 1 are dissolved in 60 ml of buffer I and the solution is loaded on to the column of FGF-SEPHAROSE ® agarose gel; the column is then washed with 600 ml of buffer I at a flow rate of 60 ml per hour. Finally, the column is eluted with buffer I adjusted to 1M NaCl.

The 20 ml of the eluate containing oligosaccharides are pooled and precipitated by the addition of 120 ml of absolute ethanol. This leads to the recovery of 0.26 mg of a mixture of octasaccharides giving rise to the elution profile from an ion exchange column shown in FIG. 6.

The $^{13}$C NMR spectrum is deuterated water at 25 MHz for the mixture of octasaccharides obtained is given in FIG. 7.

EXAMPLE 7

Preparation of decasaccharides with high affinity for anionic FGF by affinity chromatography on FGF-SEPHAROSE ® agarose gel.

The chromatographic column is prepared as described in example 1 D.

300 mg of the decasaccharide fraction such as that obtained in example 1 are dissolved in 60 ml of buffer I and the solution is loaded on to the column of FGF-SEPHAROSE ® agarose gel; the column is then washed with 600 ml of buffer I at a flow rate of 60 ml per hour. Finally, the column is eluted with buffer I adjusted to 1M NaCl.

The 26 ml of the eluate containing oligosaccharides are pooled and precipitated by the addition of 160 ml of absolute ethanol. This leads to the recovery of 0.38 mg of a mixture of decasaccharides giving rise to the elution profile from an ion exchange column shown in FIG. 8.

The $^{13}$C NMR spectrum is deuterated water at 25 MHz for the mixture of decasaccharides obtained is given in FIG. 9.

EXAMPLE 8

Preparation of a Mixture of Fragments of Glycosaminoglycans with an Affinity for the Anionic FGF The procedure is the same as that described in example 1 except that the gel filtration step C is omitted.

Affinity chromatography on FGF-SEPHAROSE ® agarose gel is then performed on a mixture containing the di-, teta-, hexa, octa-, deca-, dodeca-, and tetradecasaccharides shown in the table in Example 1, C-GEL filtration section.

This chromatographic step leads to the isolation of those chains of the mixture which are endowed with an affinity for FGF.

EXAMPLE 9

120 mg of hexasaccharides are prepared according to the procedure described in example 3 above, with the omission of the reduction step with sodium borohydride subsequent to the initial deploymerization of heparin described in example 1.

These 120 mg of hexasaccharides are dissolved in 100 ml of 0.5M NaCl. 50 ml of aminoethyl -SEPHAROSE ® agarose gel are added (containing about 8 µmoles of aminoethyl group per ml of decantered matrix and 50 mg of sodium cyanoborohydride. The reaction mixture is brought to pH 11 by the addition of 5N sodium hydroxide solution and agitated gently at room temperature for 10 days.

The matrix is then filtered off on a Buchner filter funnel, washed with 1 liter of 0.5M NaCl solution, pH 7, then with 1 liter of $10^{-3}$N hydrochloric acid, then with 500 ml of 1M NaCl, pH 10.0 and finally with 1 liter of distilled water.

A 5 ml aliquot of the matrix is sampled and hydrolyzed for 3 hours at 100° C. in 2N hydrochloric acid. Analysis of the uronic acids in the hydrolysate shows that the matrix finally obtained contains 2 mg of hexasaccharides bound in a covalent manner per ml of SEPHAROSE ® agarose gel.

40 ml of the hexasaccharide-SEPHAROSE® agarose gel matrix are placed in a column 2.5 cm in diameter and 8 cm high.

The column is equilibrated with 0.02M Tris-HCl buffer, pH 7.0, containing 0.3M NaCl (buffer I).

2 mg of anionic FGF from beef brain (prepared according to the method of R. R. Lobb and J. W. Fett, Biochemistry, vol. 23, No. 26, 1984, p. 6295–6299), are dissolved in 10 ml of buffer I and allowed to percolate in to the column which is then rinsed with 120 ml of the same buffer I.

The column is then eluted with a linear gradient obtained by the progressive mixing of 200 ml of buffer I and 200 ml of 0.02M Tris-HCl buffer, pH 7.0, containing 2M NaCl.

The peak of anionic FGF emerges from the column at an ionic strength of about 0.7M, and is recovered in 95% yield.

EXAMPLE 10

10 mg of decasaccharides are prepared according to the method described in example 7 above, with the omission of the reduction step with borohydride subsequent to the initial depolymerization of heparin as described in example 1.

These 10 mg of decasaccharides are dissolved in 20 ml of distilled water. 5 ml of aminoethyl -SEPHAROSE® agarose gel are added (containing 8 $\mu$moles of aminoethyl group per ml) and 5 mg of sodium cyanoborohydride. The pH of the suspension is adjusted to pH 11 by the addition of 5N sodium hydroxide solution and agitated gently for one week at room temperature.

The SEPHAROSE® agarose gel matrix is then filtered off on to a Buchner filter funnel, washed with 100 ml of 0.5M NaCl solution, pH 7, then with 100 ml of $10^{-3}$N hydrochloric acid, followed by 100 ml of 2M NaCl and finally with 200 ml of distilled water.

1 ml of the matrix is sampled and hydrolysed for 3 hours in 5 ml of 2N hydrochloric acid. Analysis of the uronic acids in the hydrolysate shows that the matrix obtained contains 1.8 mg of decasaccharides bound covalently per ml of SEPHAROSE® agarose gel.

4 ml of decasaccharide-SEPHAROSE® agarose gel are placed in a column 1 cm in diameter and 5 cm high. The column is equilibrated with 0.02M Tris-HCl buffer, pH 7.0, containing 0.6M NaCl (buffer II). 0.2 mg of anionic FGF from beef brain prepared by the same method as that cited in example 1 are dissolved in 2 ml of buffer II and loaded on to the top of the column. The column is rinsed with 40 ml of buffer II. Elution is then performed with 0.02M Tris-HCl buffer, pH 7.0, containing 2M NaCl. The anionic FGF is eluted as a sharp peak. The quantity recovered in the eluate amounts to about 0.18 mg, corresponding to a yield of 90%.

EXAMPLE 11

According to a variant of the procedure described in example 1, the depolymerization step is performed by periodate oxidation which is carried out as follows:

1)—Cleavage of Heparin Chains by Means of Periodic Acid 10 g of injectable heparin from porcine mucus in the form of its sodium salt and titrating at 157 IU/mg in the Codex analysis and 155 U/mg in the anti-factor Xa analysis of Yin et al., are dissolved in 250 ml of demineralized water at 4° C. The pH of the solution is adjusted to 5.0 by the addition of concentrated hydrochloric acid. 10 g of sodium metaperiodate (NaIO$_4$, MW: 213.89) dissolved in 250 ml of demineralized water at 4° C. are added with gentle stirring. The pH of the mixture is adjusted to 5.0 by the addition of concentrated hydrochloric acid. The solution is left in the dark in the cold room at 4° C. for 24 hour.

2)—Removal of Residual Periodate

The reaction solution is then distributed between 3 sacs of NOJAX 40® dialysis tubing (porosity from 3 to 4000 Da) and dialyzed for 15 hours against running demineralized water.

3)—Depolymerization in Basic Medium

To the 780 ml of solution obtained after dialysis, are added 16 ml of 10N sodium hydroxide solution, and the solution is then stirred for 3 hours at room temperature (about 18°–21° C.).

If need be, this step is followed by a reduction which is carried out as follows:

500 mg of sodium borohydride (NaBH$_4$, MW: 37.83) are then added and the solution is stirred for a further 4 hours at room temperature. The pH is then brought to 4 by the addition of concentrated hydrochloric acid. After the solution has been stirred for 15 minutes, the pH is adjusted to 7 by the addition of concentrated sodium hydroxide.

To the 820 ml of solution thus obtained are added 16.4 g of NaCl, then 1270 ml of ethanol.

The mixture is allowed to stand for 3 hours, then it is centrifuged at 2500 rpm for 20 minutes.

The precipitate is collected, resuspended in 200 ml of absolute ethanol, disintegrated with ULTRA-TURRAX® apparatus for dispersing at high frequencies and finally isolated by filtration on a fritted Buchner funnel. It is then dried in a vacuum at 40° C. for 5 hours.

This leads to the recovery of 8.9 g of a degradation product having the following properties:

Codex analysis: 8 IU/mg
APTT analysis: 7 IU/mg
AntiXa analysis: 8 U/mg

The mixture of chains obtained is subject to gel filtration as described in example 1.

EXAMPLE 12

Toxicity

IC 1696, 1701 and 1702 were administered to mice subcutaneously and intravenously over a period of 15 days and did not show any toxicity. For both routes of administration, the LD 50 is higher than 2 g/kg.

EXAMPLE 13

Activity of the Products of the Invention on a Cell Culture System

A—Description of the System

LE II cells (endothelial cells of mouse lung) are cultivated on plates containing 24 wells in the presence of 10% foetal calf serum until ¾ of confluence is attained.

The cells are then maintained for 48 hours in only 0.2% serum and rendered quiescent.

The growth medium is then supplemented with either fibroblast growth factor (FGF) or the oligosaccharide fragments to be tested or both products simultaneously (FGF + product to be tested).

The culture is maintained for a further 24 hours and tritiated thymidine is added 4 hours before the end of the experiment.

The radioactivity incorporated is then counted; each measurement is made in triplicate.

B—Results

Figure 10:
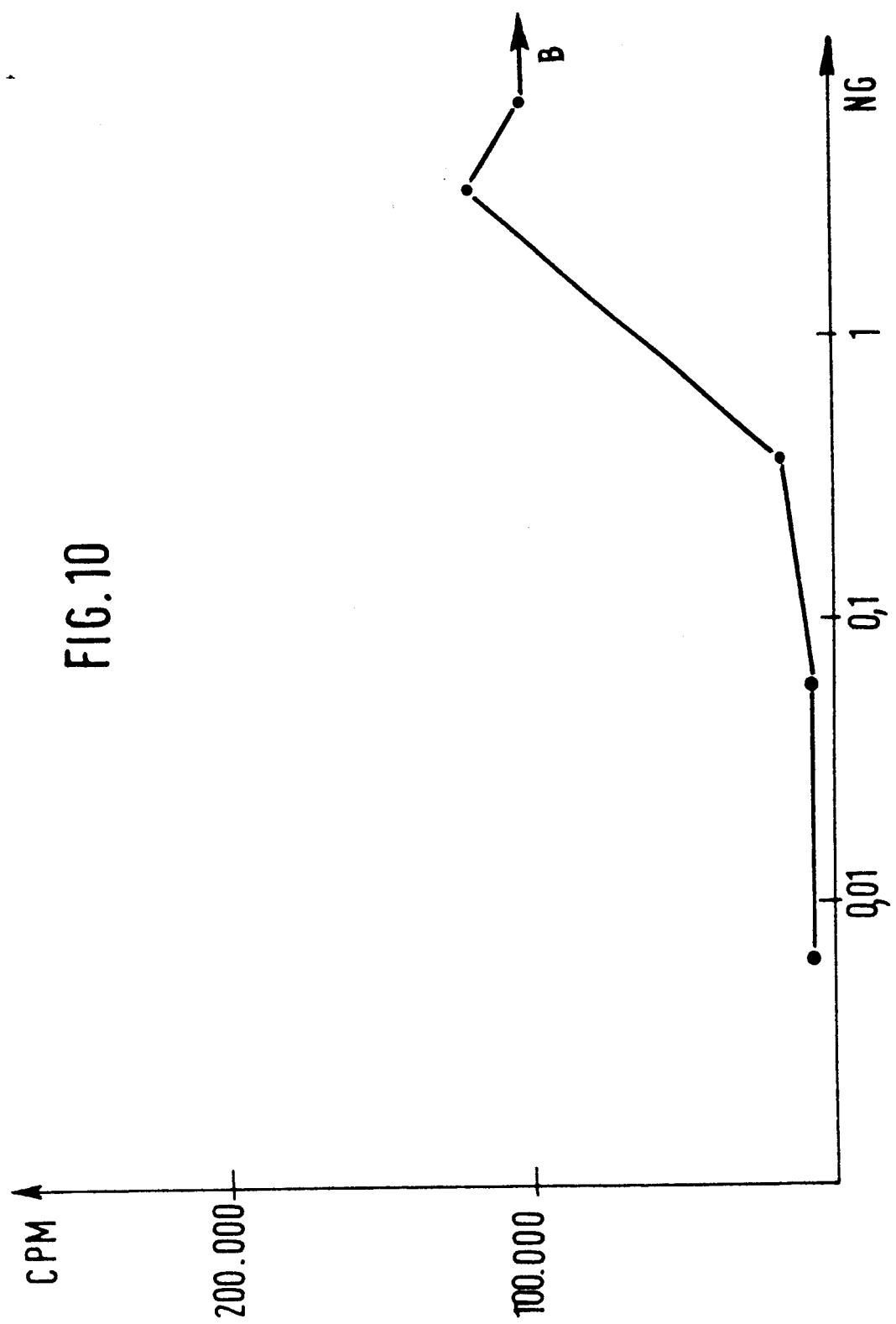

They are given in the following figures:

FIG. 10, dose-response curve in the presence of anionic FGF alone.

The plateau obtained after stimulation is situated at 126,000 cpm for a dose of 5 ng/ml. In the figures which follow, maximal stimulation in the presence of anionic FGF alone is represented by the dotted line.

The curve Δ____Δ representing the results obtained when the glycosaminoglycan is used along and the curves ·____· those obtained when the glycosaminoglycan is used together with the anionic FGF.

Figure 11:
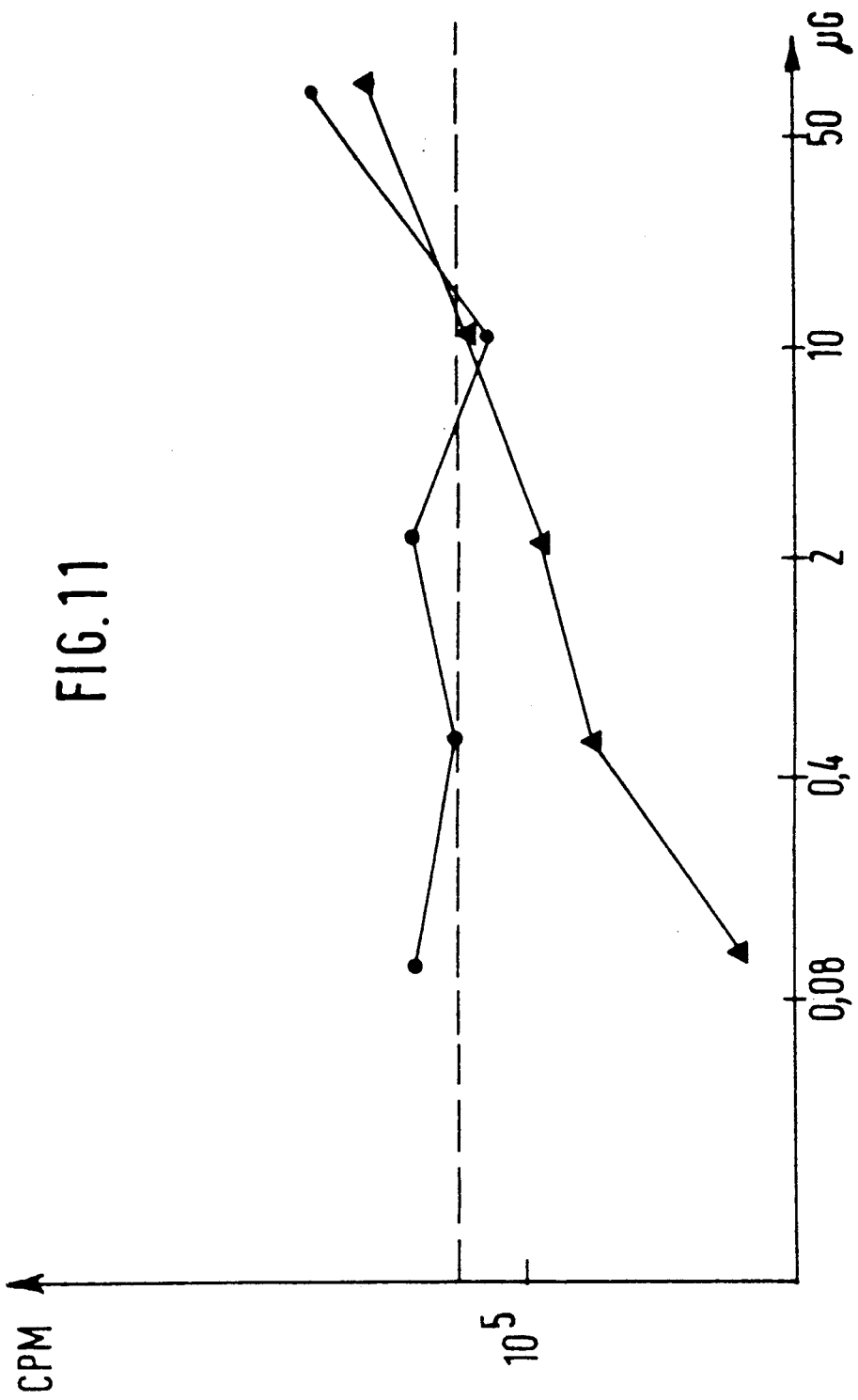

FIG. 11, dose-response curve in the presence of the hexasaccharide IC 1696, alone or together with thee anionic FGF (5 ng/ml).

It will be observed that IC 1696 possesses a dose-dependent activity over the range 0.08 to 50 μg/ml of culture medium.

When combined with anionic FGF an increase in activity compared with that of FGF alone is observed above a dose of 10 μg/ml.

Under the experimental conditions and in this cell system, IC 1696 potentiates the activity of the anionic FGF.

Figure 12:
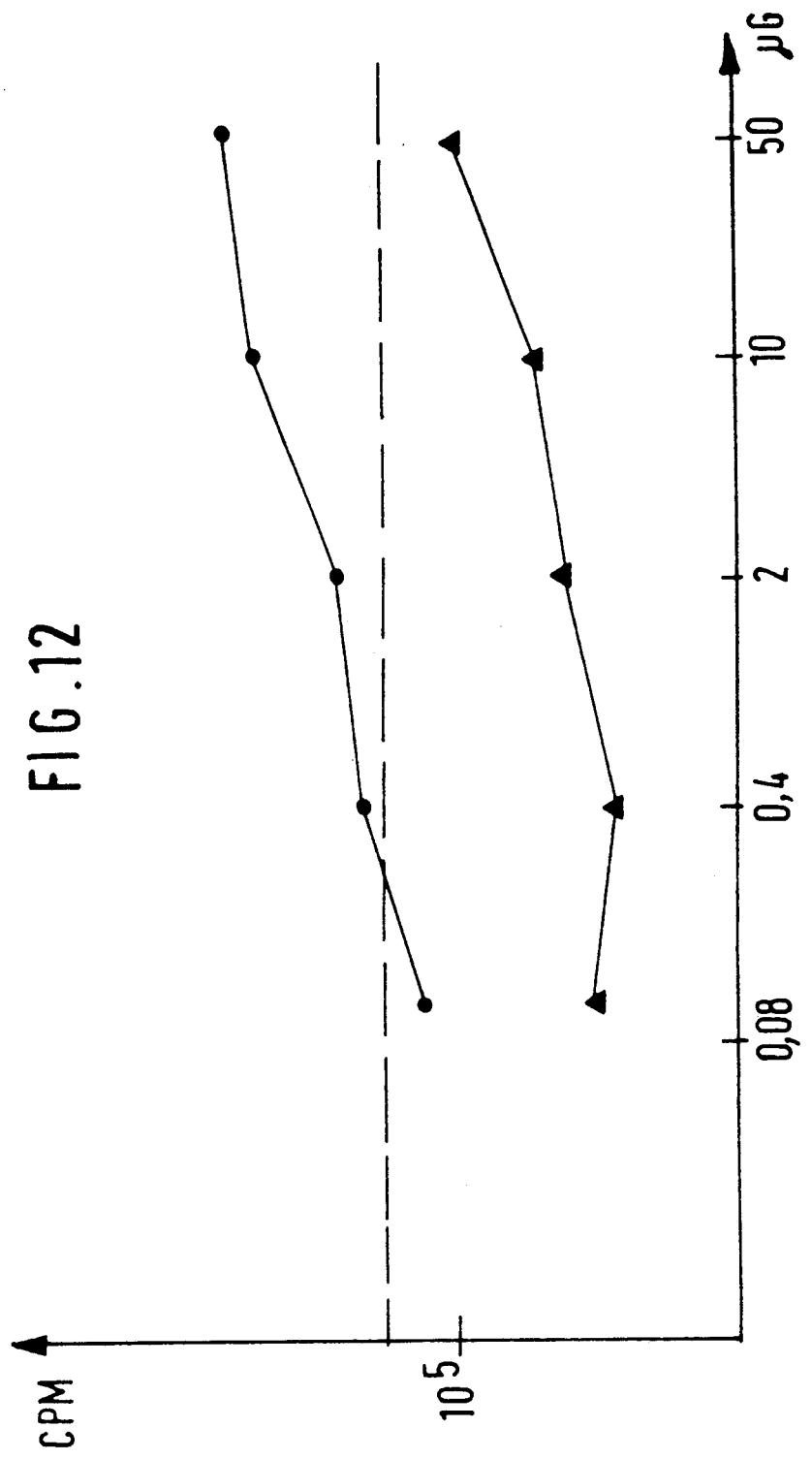

FIG. 12, dose-response curve in the presence of the hexasaccharide IC 1697, alone or together with the anionic FGF (5 ng/ml).

IC 1697 used alone shows dose-dependent activity between 0.04 and 50 μg/ml.

Used in combination with the anionic FGF, under the conditions of the model system it markedly potentiates activity above a dose of 0.4 μg/ml.

Figure 13:
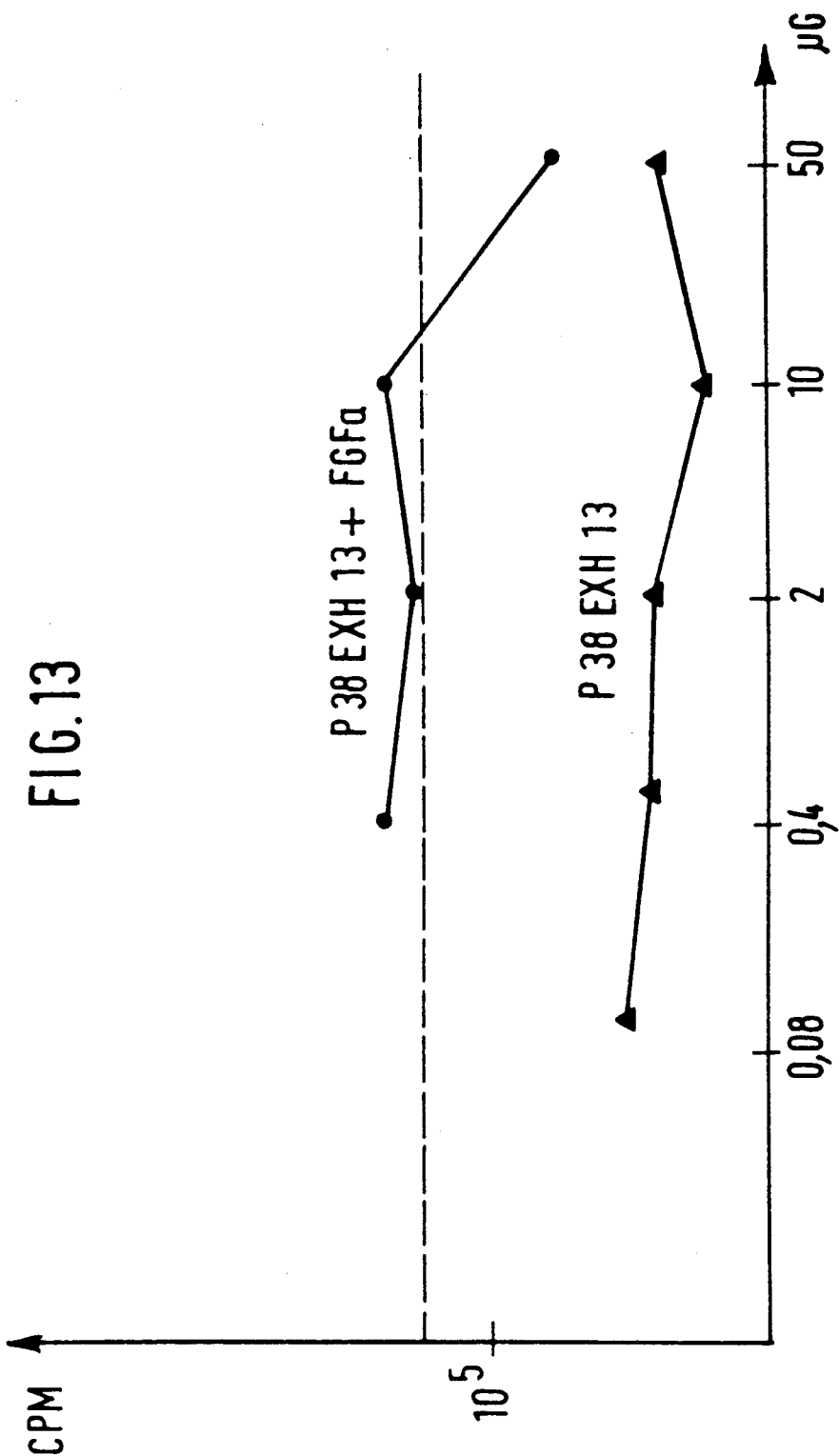

FIG. 13, dose-response curve in the presence of a reference substance lacking affinity for the anionic FGF: The hexasaccharide P 38 EXH 13, alone or together with the anionic FGF (5 ng/ml).

The fragment used as reference does not show any significant activity when it is used alone.

In conclusion, in this experimental model (quiescent cells in the absence of serum), the oligosaccharides possessing an affinity for FGF have a stimulating (mitogenic) effect.

EXAMPLE 14

Activity of the Oligosaccharides on the Proliferation of Endothelial Cells of Bovine Aorta in the Presence of Basic FGF Endothelial cells of bovine aorta are inoculated at low density (20,000 cells per 35 mm dish) in modified Eagle medium containing 10% foetal calf serum.

The cells are maintained in culture for 4 days and supplemented at day D. O. nd D=2 with 10 μl of a basic solution containing FGF at a concentration of 8.6 pg/μl.

Furthermore, at day D. O., the cultures are supplemented with varying concentrations of the oligosaccharides to be tested. After 4 days, the cells are counted by means of a Coulter cell counter.

The results are expressed as percentage inhibition of the proliferation of the cells in comparison with cultures which had not been treated with the products under test. For comparative purposes, assays were also carried out with heparin.

The results obtained are as follows:

They are expressed as ED 50, i.e. the amount of product which is necessary to inhibit by 50% the cell proliferation in cultures receiving only FGF:

| Products tested | ED 50 |
| --- | --- |
| IC 1696 | 1 μg/ml |
| IC 1701 | 1.8 μg/ml |
| IC 1702 | 40 μg/ml |
| Heparin | 1 μg/ml |

For comparative purposes, the activity of regular tetrasaccharides and disaccharides, obtained by gel filtration and ion exchange chromatography after depolymerization with nitrous acid, was also tested. It was observed that these products, lacking affinity for FGF, exhibited no inhibitory activity in the test system.

In contrast, IC 1696 and IC 1701 have about the same activity as heparin and IC 1702 is very much more active.

EXAMPLE 15

Effect of the Oligosaccharides on the Proliferation of Human Endothelial Cells in Culture Primary cultures of endothelial cells of the umbilical vein are prepared according to the procedure of Jaffe (J. Clin. Invest., 1973, 52, 2745). At confluence (5–7 days), the cells are detached by an EDTA-trypsin mixture. They are then re-inoculated on Falcon plates of 24 wells, covered beforehand with fibronectin (5 μg/cm$^2$), at a density of 5,000 cells/cm$^2$ in 199 medium supplemented with 20% foetal calf serum (FCS).

24 hours later, the medium is replaced by 199 medium supplemented with 10% FCS and the glycosaminoglycans are added alone or in combination with acidic FGF (FGFa). 48 hours latter, growth factor is added again. After 4 days of culture, the cells are detached by the EDTA-trypsin mixture and the cells are counted by means of a cell counter (Coulter Counter ® Coultronics). Each experimental curve (FIG. 14A–D) represents a typical experiment conducted in triplicate. Each experiment is repeated 2 to 3 times.

In the FIGS. 14A–D, the dotted line represents the basal proliferation of a culture containing 10% FCS without FGFa and without oligosaccharide; the curve shown as ·____·____· represents control in the presence of FGFa alone; the curves ____ ____ and ____ ____ represent the results obtained in the presence of FGFa combined with concentrations of 1 μg/ml and 5 μg/ml of heparin, or of 10 μg/ml and 50 μg/ml of oligosaccharides, respectively.

Under our experimental conditions, FGFa in the absence of oligosaccharides induces a maximal increase of 230% of the number of cells compared with that found in the presence of FCS alone at a concentration of 10%, the ED 50 is about 7 ng/ml. By ED 50 is understood that concentration of FGFa (ng/ml) which induced 50% of the maximal proliferation obtained with 50–100 ng/ml of FGFa.

RESULTS

The effects of the oligosaccharides were examined in comparison with the starting heparin as standard (batch 91416).

Figure 14:
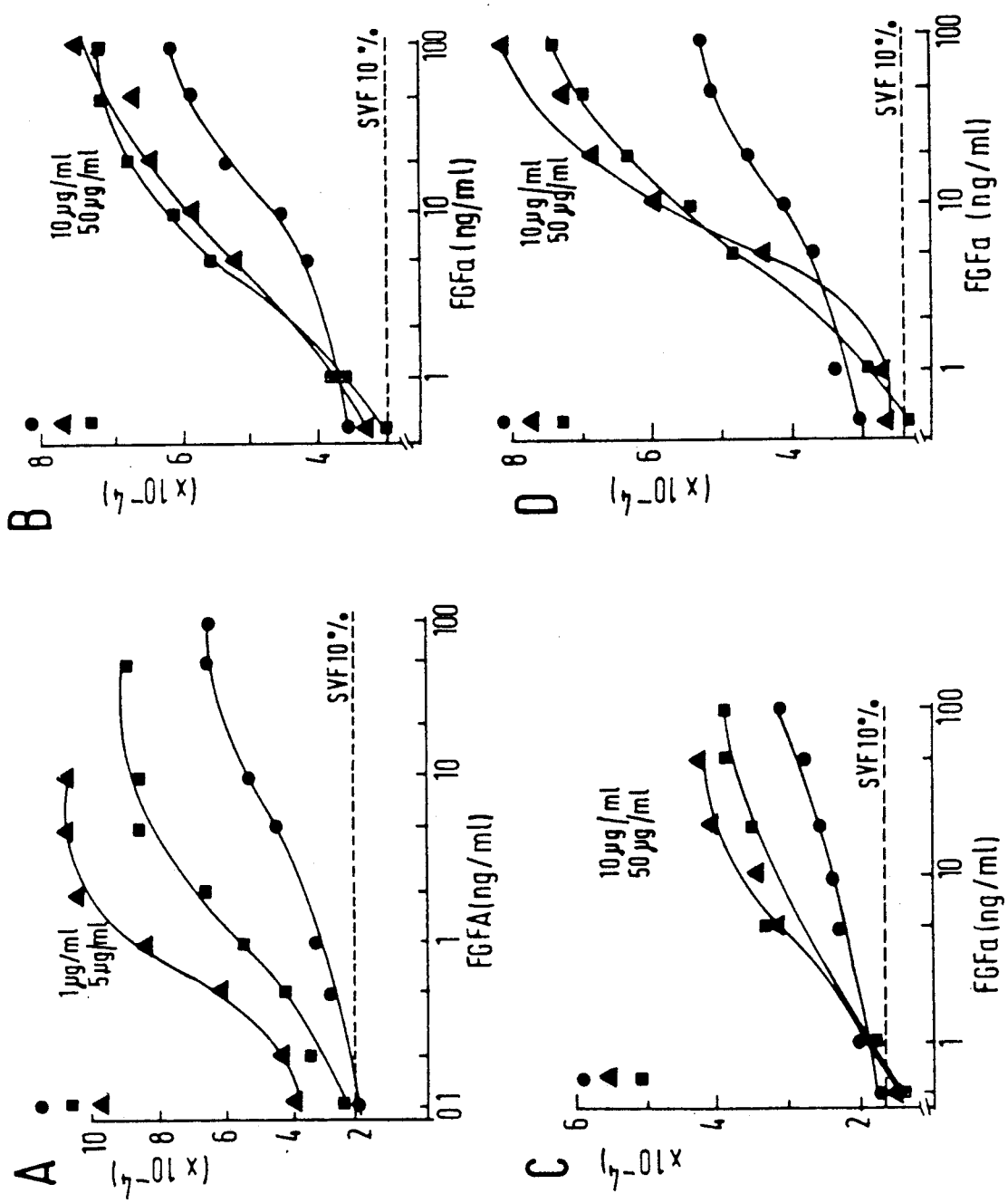

Under the experimental conditions chosen, heparin potentiates the effect of FGFa. This potentiating effect begins at a concentration of heparin of 200 ng/ml and reaches its maximum at a concentration of heparin of 25 μg/ml. A concentration of heparin of 1 μg/ml diminishes the ED 50 of FGFa ten times (FIG. 14A). It is observed that the oligosaccharides tested display different effects depending on the experimental conditions used.

1) In the absence of FGFa, at a concentration of 1 to 100 μg/ml, the oligosaccharides inhibit the growth of the endothelial cells (Table below).

INHIBITORY EFFECT OF GLYCOSAMINOGLYCANS ON THE GROWTH OF HUMAN ENDOTHELIAL CELLS IN THE PRESENCE OF FCS AND IN THE ABSENCE OF FGFa

| | INHIBITION (%) | | |
|---|---|---|---|
| | 1 μg/ml | 10 μg/ml | 100 μg/ml |
| Hexasaccharide IC 1696 | 8,4 | 25,5 | 34,9 |
| Octosaccharide IC 1701 | 5,9 | 25,4 | 19,5 |
| Decasaccharide IC 1702 | 11,0 | 22,4 | 10,0 |

2) At concentrations of FGFa higher than the ED 50 (7 ng/ml), a stimulating effect of the oligosaccharides on cell growth is observed (FIG. 14B-D). This effect requires higher concentrations of oligosaccharides than of heparin. The most active product is the decasaccharide IC 1702 (at 70 μg/ml, the ED 50 is lowered to 3.2 μg/ml). The hexasaccharide IC 1696 has a very weak effect on the stimulation of cell growth. The property of potentiating FGFa shows good correlation with the affinity of these oligosaccharides for the growth factor.

In conclusion, the test used demonstrates two effects of the oligosaccharides: an inhibitory effect in the presence of serum and in the absence of FGFa, and a stimulating effect in the presence of the growth factor for which they have an affinity. This suggests a modulating role of the glycosaminoglycans on cell growth. The inhibitory effect suggests the possibility of an action counteracting angiogenesis in vivo. The stimulating effect, in combination with the growth factor, suggests that these products may be used either to stabilize and to potentiate the growth factor or to stimulate tissue repair.

The activity of the hexasaccharide IC 1696 was tested on an angiogenesis model adapted from J. Folkman et al. (Science, 1983, 221, 719), the impregnated implants of polymer being replaced by intravenous injections of the product to be tested.

The rabbits were given two intravenous injections per day of 10 mg/kg of the hexasaccharide IC 1696 dissolved alone or in combination with steroids in isotonic sodium chloride solution.

In the animals treated with IC 1696 a much less marked vascularization is observed than in the animals which have simply been given the isotonic sodium chloride solution; in particular, in the former, the secondary vascularization is much less developed.

In a preliminary experiment using the same model system, IC 1696 alone showed an inhibitory action on angiogenesis.

We claim:

1. A process for obtaining high anionic strength heparinic oligosaccharides from a mixture of heparinic glycosaminoglycans, which mixture of heparinic glycosaminoglycans is substantially free of non-heparin components and is produced by the depolymerization of heparin, comprising the steps of:
    contacting the mixture of glycosaminoglycans with a cationic or anionic cell growth factor to bind said oligosaccharide to the growth factor; and then
    eluting said heparinic oligosaccharides from the growth factor.

2. The process of claim 1, wherein the growth factor is anionic and is bound to a support.

3. The process of claim 2, wherein the support is an agarose support.

4. The process of claim 1, wherein the mixture of glycosaminoglycans contains chains of saccharide residues which do not have a binding site for AT III.

5. The process of claim 4, wherein the mixture of glycosaminoglycans contains chains containing a maximum of 14 saccharide residues selected from the group consisting of chains with an α,β- unsaturated uronic acid residue at a non-reducing end and chains with a residue possessing a 2,5 anhydromanno structure at a reducing end.

6. The process of claim 1, wherein the mixture of glycosaminoglycans is loaded on a chromatographic column containing a cationic or anionic growth factor fixed to an agarose support; the column being equilibrated with a buffer having an ionic strength corresponding to that of 0.2M NaCl; and then, the oligosaccharide retained on the support is eluted from the column with a buffer having an ionic strength corresponding to that of 1M to 2M NaCl.

7. The process of claim 6, wherein the mixture of glycosaminoglycans is homogeneous with regard to the molecular weight of the glycosaminoglycans.

8. The process of claim 1, wherein the mixture of glycosaminoglycans is subjected to ion exchange chromatography on a strongly basic anion exchange column of the quaternary ammonium type and an ionic strength gradient is set up in the elution buffer by varying the concentration of NaCl in the buffer from 0.5±0.1M to 1 to 2M, and the most anionic fractions are recovered.

9. The process of claim 8, wherein the mixture of glycosaminoglycans is obtained by depolymerization of heparin, followed by alcoholic fractionation in order to separate chains endowed with an antithrombin III affinity from chains lacking said affinity.

10. The process of claim 1 wherein a heparinic hexasaccharide is obtained in a fraction eluted in a volume between 32L and 36L of eluant from a gel filtration column wherein: 60 g of precipitate, obtained by alcoholic precipitation of a nitrous acid depolymerization mixture of heparin, was taken up in 500 ml of 0.5M NaCl solution and loaded on to a 100 cm×25 cm column containing 45 liters of agarose-acrylamide, equilibrated with a 0.5M NaCl buffer, pH 6.0, and elution was carried out at a flow rate of 1500 ml/hour; a product obtained was separated by affinity chromatography on anionic FGF SEPHAROSE ® agarose gel using a 2.5 cm×6.5 cm column containing 30 ml of anionic FGF-SEPHAROSE ® agarose gel and equilibrated with 0.01M Tris-HCL buffer, pH 7.4, containing 0.2M NaCl; 300 mg of the product in a solution of 60 ml of the Tris-HCl buffer was loaded on to the column and elution was carried out with this Tris-HCl buffer adjusted to 1M NaCl; and the hexasaccharide was recovered from a fraction collected by precipitation with ethanol.

11. The process of claim 1 wherein a heparinic octasaccharide is obtained in a fraction eluted in a volume between 28 L and 32L of eluant from a gel filtration column wherein: 60 g of precipitate, obtained by alcoholic precipitation of a nitrous acid depolymerization mixture of heparin, was taken up in 500 ml of 0.5M NaCl and loaded on to a 100 cm×25 cm column containing 45 liters of agarose-acrylamide and equilibrated with a 0.5M NaCl buffer, pH 6.0, and elution was carried out at a flow rate of 1500 ml/hour; a product obtained was separated by affinity chromatography on anionic FGF SEPHAROSE® agarose gel using a 2.5 cm×6.5 cm column containing 30 ml of anionic FGF SEPHAROSE® agarose gel and equilibrated with a 0.01M Tris-HCL buffer, pH 7.4, containing 0.2M NaCl; 300 mg of the product dissolved in 60 ml of the Tris-HCl buffer was loaded on to the column and elution was carried out with the Tris-HCl buffer adjusted to 1M NaCl; and the octasaccharide was recovered from a fraction collected by precipitation with ethanol.

12. The process of claim 1 wherein a heparinic decassacharide is obtained in a fraction eluted in a volume between 25L and 28 L of eluant from a gel filtration column wherein: 60 g of precipitate, obtained by alcoholic precipitation of a nitrous acid depolymerization mixture of heparin, was taken up in 500 ml of 0.5M NaCl solution and loaded on to a 100 cm×25 cm column containing 45 liters of agarose-acrylamide, equilibrated with a 0.5M NaCl buffer, pH 6.0, and elution was carried out at a flow rate of 1500 ml/hour: and a product obtained was separated by affinity chromatography on anionic FGF SEPHAROSE® agarose gel using a 2.5 cm×6.5 cm column containing 30 ml of anionic FGF-SEPHAROSE® agarose gel and equilibrated with 0.01M Tris-HCL buffer, pH 7.4, containing 0.2M NaCl; 300 mg of the product in a solution of 60 ml of the Tris-HCl buffer was loaded to the column and elution was carried out with the Tris-HCl buffer adjusted to 1M NaCl; and the decasaccharide was recovered from a fraction collected by precipitation with ethanol.

* * * * *